United States Patent
Gu et al.

(10) Patent No.: US 10,981,991 B2
(45) Date of Patent: Apr. 20, 2021

(54) PD-1 ANTIBODIES AND USES THEREOF

(71) Applicant: ASIA BIOTECH PTE. LTD., Singapore (SG)

(72) Inventors: Nana Gu, Hong Kong (CN); Ke Shao, Singapore (SG)

(73) Assignee: SHANGHAI ZHANGJIANG BIOTECHNOLOGY CO., LTD., Shanghai (CN)

(*) Notice: Subject to any disclaimer, the term of this patent is extended or adjusted under 35 U.S.C. 154(b) by 416 days.

(21) Appl. No.: 15/764,494

(22) PCT Filed: Sep. 29, 2016

(86) PCT No.: PCT/SG2016/050482
§ 371 (c)(1),
(2) Date: Mar. 29, 2018

(87) PCT Pub. No.: WO2017/058115
PCT Pub. Date: Apr. 6, 2017

(65) Prior Publication Data
US 2018/0282412 A1    Oct. 4, 2018

Related U.S. Application Data

(60) Provisional application No. 62/234,076, filed on Sep. 29, 2015.

(51) Int. Cl.
*C07K 16/28* (2006.01)
*A61K 39/395* (2006.01)
*C07K 14/705* (2006.01)
*C07K 16/46* (2006.01)
*C07K 19/00* (2006.01)
*A61P 31/00* (2006.01)
*A61P 35/00* (2006.01)

(52) U.S. Cl.
CPC ........ *C07K 16/2818* (2013.01); *A61K 39/395* (2013.01); *C07K 14/70503* (2013.01); *C07K 16/46* (2013.01); *C07K 19/00* (2013.01); *A61P 31/00* (2018.01); *A61P 35/00* (2018.01); *C07K 2317/24* (2013.01); *C07K 2317/33* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| WO | 2006121168 A1 | 11/2006 |
| WO | 2008156712 A1 | 12/2008 |
| WO | 2011110621 A1 | 9/2011 |
| WO | 2014194302 A2 | 12/2014 |
| WO | 2015112800 A | 7/2015 |

OTHER PUBLICATIONS

Malia et al (Proteins, 84;427-434, 2016).*
Gardiner, David, et al., "A randomized, double-blind, placebo-controlled assessment of BMS-936558, a fully human monoclonal antibody to programmed death-1 (PD-1), in patients with chronic hepatitis C virus infection." PloS ONE, May 22, 2013, vol. 8, No. 5, pp. e63818:1-11.
Porichis, Filippos, et al., "Role of PD-1 in HIV pathogenesis and as target for therapy." Current HIV/AIDS Reports Mar. 2012, vol. 9, No. 1, pp. 81-90.
Berger, Raanan, et al. "Phase I safety and pharmacokinetic study of CT-011, a humanized antibody interacting with PD-1, in patients with advanced hematologic malignancies." Clinical Cancer Research, May 15, 2008, vol. 14, No. 10, pp. 3044-3051.
Chu, Fuliang, et al. "Anti-PD-1 antibodies for the treatment of B-cell lymphoma" Oncoimmunology, Feb. 14, 2014, vol. 3, No. 3, pp. e28101:1-3.
International Application No. PCT/SG2016/050482, International Search Report and Written Opinion dated Nov. 18, 2016.
Singapore Application No. 11201802644W, Written Opinion dated Sep. 27, 2018, 6 pages.

* cited by examiner

*Primary Examiner* — Brad Duffy
(74) *Attorney, Agent, or Firm* — Kilpatrick Townsend & Stockton LLP

(57) ABSTRACT

The present invention provides monoclonal antibodies that specifically bind to human PD-1 with high affinity. Nucleic acid molecules encoding the antibodies of the invention, expression vectors, host cells and methods for expressing the antibodies of the invention are also provided. The PD-1 antibodies of the present invention inhibit the binding of PD-L1 to PD-1, thereby modulating immune responses in general, and those mediated by TcR and CD28, in particular. The invention also provides methods for treating various diseases, including infectious diseases and cancer using the PD-1 antibodies of the present invention.

16 Claims, 14 Drawing Sheets

Specification includes a Sequence Listing.

FIG. 1
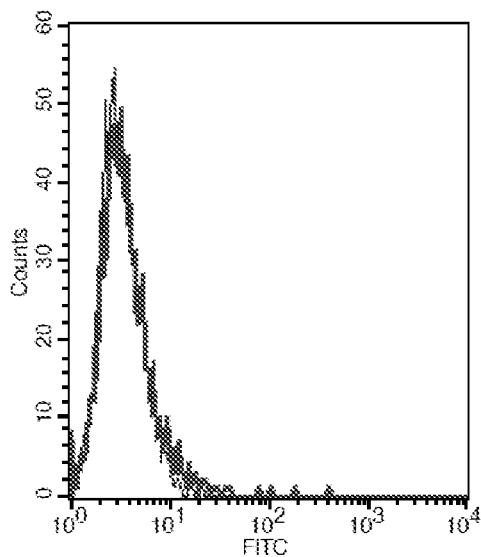
A CHO cells
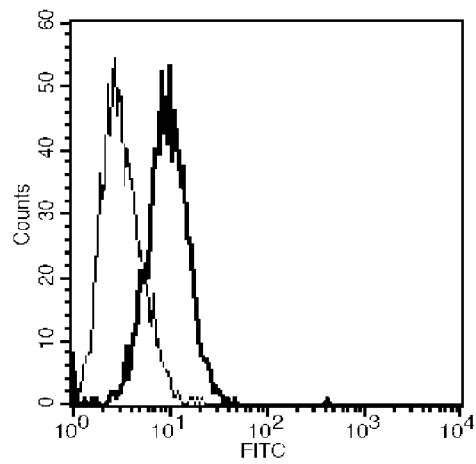
B CHO/PD-1 cells

```
             1         10        20        30        40        50 a      60
67D9VH     EVILVESGGGLVKPGGSLKVSCAASGFTFS [TYGMS] WVRQTPEKRLEWVA [TISGGGRDTYYPD-
humIII     EVQLVESGGGLVQPGGSLRLSCAASGFTFS [SYAMS] WVRQAPGKGLEWVS [VISGDGGSTYYAD-
hu67D9VH   ------------------------------ [T-G--] --------------A [----G-RD---P-

70        80 abc    90        100abc    110
67D9VH     TVKG] RFTISRDNAKNTLYLQMSSLRSEDTALYYCAR [QDYGNYVWFAY] WGQGTLVTVSA-
humIII     SVKG] RFTISRDNSKNTLYLQMNSLRAEDTAVYYCAR [G-------FDY] WGQGTLVTVSS-
hu67D9VH   T---] ----------------S--------------- [QDYGNYVW-A-] ------------
```

B

```
             1         10        20        27abcd 30   40       50
67D9VL     DIVLTQSPASLAVSLGQRATISC [RASESVDSYGISFMH] WFQQKPGQPPQLLIY [STSNRGS] G-
humKIII    DIVLTQSPASLAVSPGQRATITC [RASESVSFLGINLIH] WYQQKPGQPPKLLIY [QASNKDT] G-
hu67D9VL   --------------S- [------DSY--SFM-] -F--------Q---- [ST--RGS] -

60        70        80        90        100
67D9VL     VPARFSGSGSGTDFSLTIHPMEEDDTAMYFC [QQSQEVPWT] FGGGTKLEIKR
humKIII    VPARFSGSGSGTDFTLTINPVEANDTANYYC [LQSKNFPWT] FGQGTKVEIKR
hu67D9VL   ---------------S--------D-----F- [Q--QEV---] -----------
```

FIG. 4
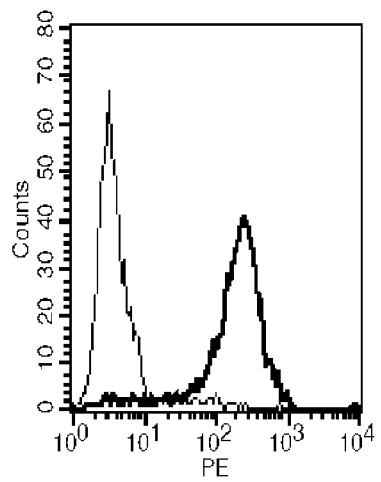
A Control IgG4
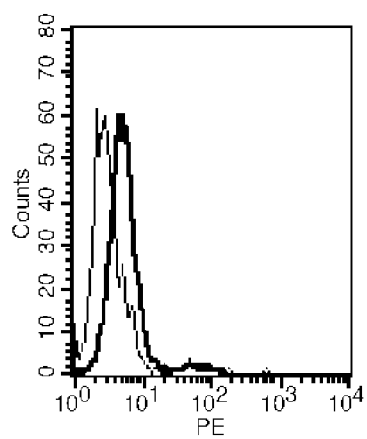 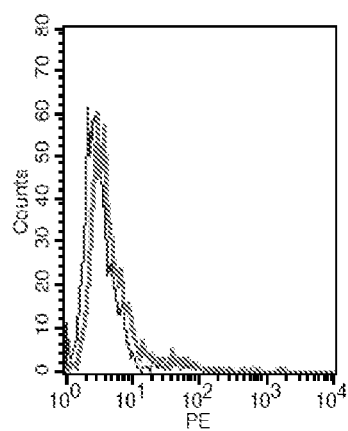 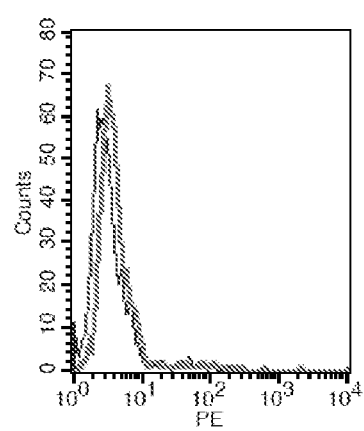
B 67D9        C c67D9        D hu67D9

Fig. 5
A
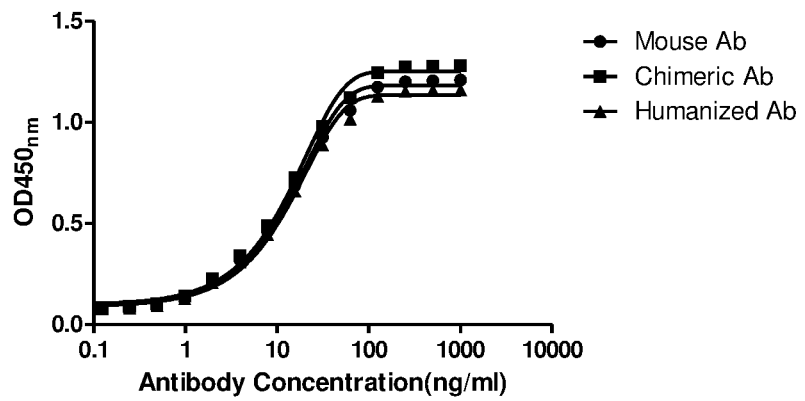
B
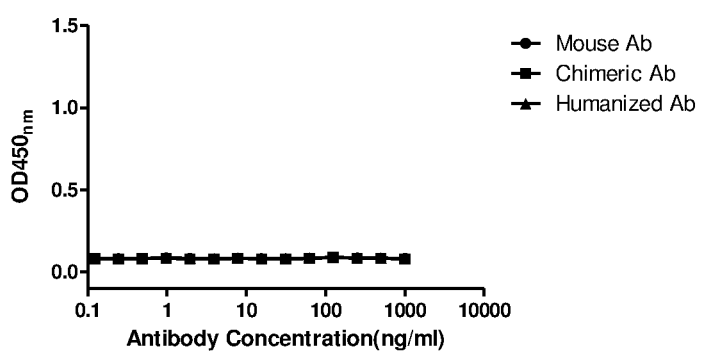
C
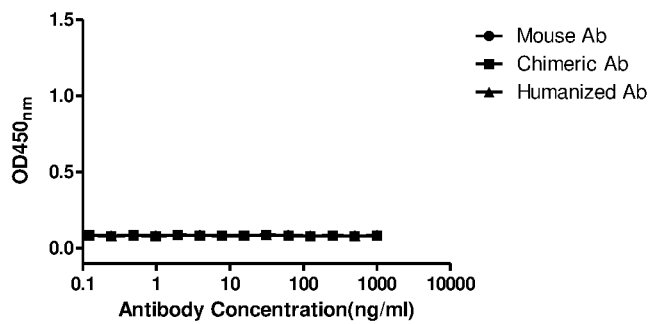
D
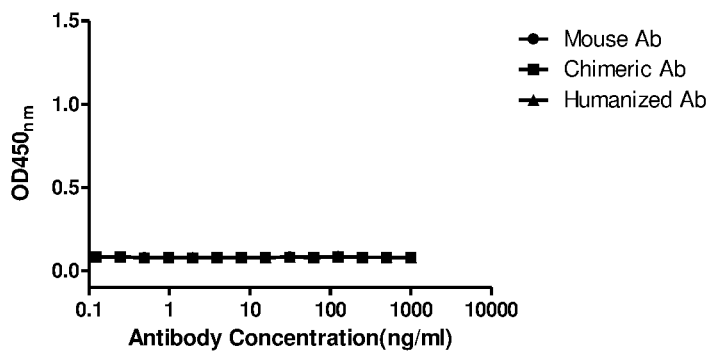

Fig. 6
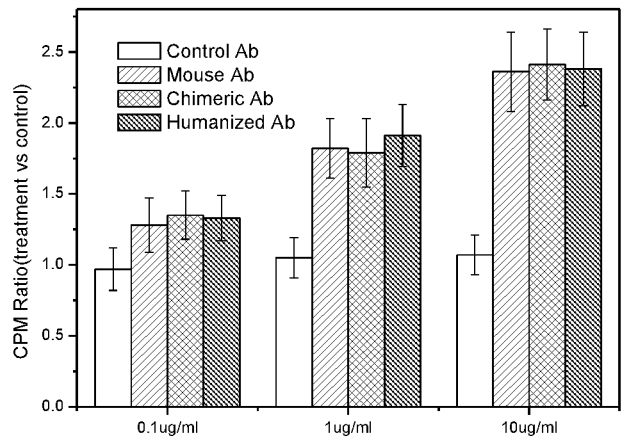
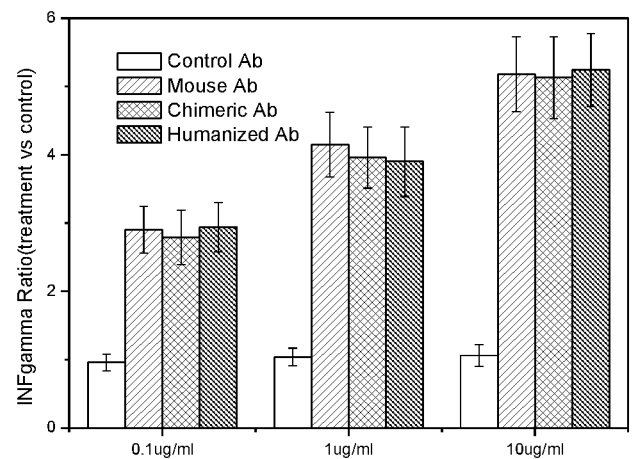
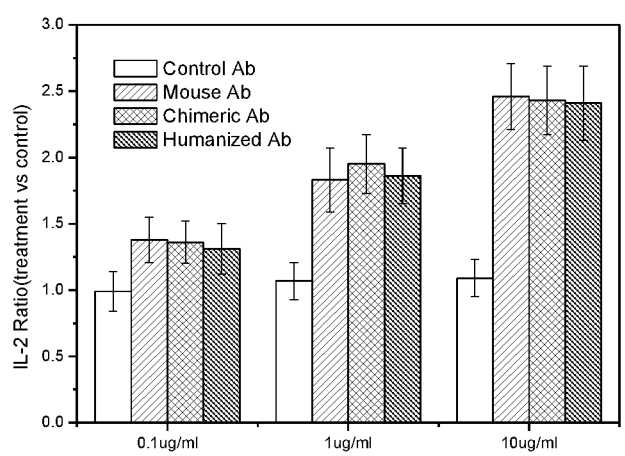

Fig 9
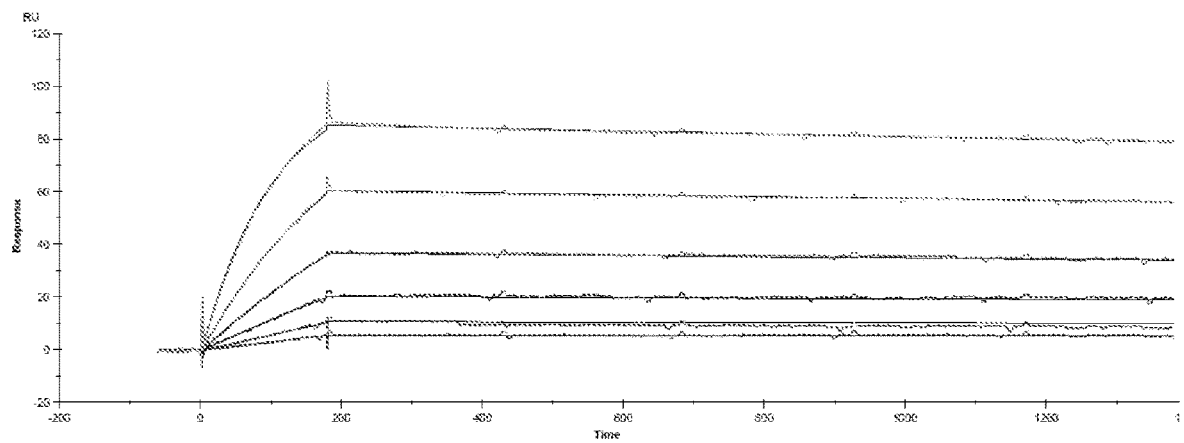
A Kinetic analysis result of Nivolumab
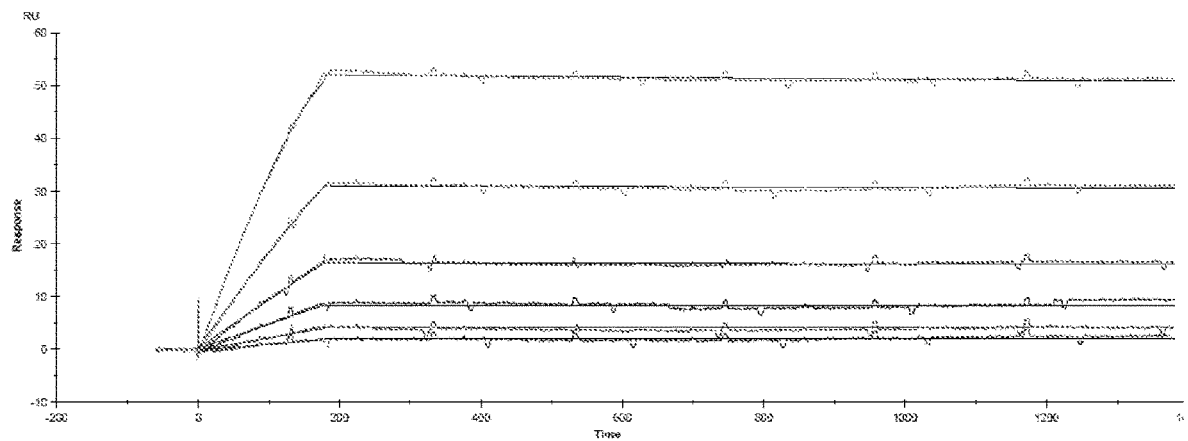
B Kinetic analysis result of hu67D9

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 1

Thr Tyr Gly Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 2

Thr Ile Ser Gly Gly Gly Arg Asp Thr Tyr Tyr Pro Asp Thr Val Lys
1               5                   10                  15

Gly
```

```
<210> SEQ ID NO 3
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 3

Gln Asp Tyr Gly Asn Tyr Val Trp Phe Ala Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Light chain CDR1

<400> SEQUENCE: 4

Arg Ala Ser Glu Ser Val Asp Ser Tyr Gly Ile Ser Phe Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Light chain CDR2

<400> SEQUENCE: 5

Ser Thr Ser Asn Arg Gly Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Light chain CDR3

<400> SEQUENCE: 6

Gln Gln Ser Gln Glu Val Pro Trp Thr
1               5

<210> SEQ ID NO 7
<211> LENGTH: 360
<212> TYPE: DNA
<213> ORGANISM: Artificial Sequence
<220> FEATURE:
<223> OTHER INFORMATION: Nucleotide sequence of hu67D9 heavy chain
      variable region

<400> SEQUENCE: 7
gaggtgcagc tcgtggaatc tgggggcgga ctggtgcagc cggtggaag tctccggctg      60 agctgcgccg ctagtgggtt cacttttct acttacggga tgtcttgggt ccgacaggca     120
ccaggcaagg ggctggagtg ggtggctact atttctggag gaggccgaga cacctactac     180
cccgacaccg tcaagggacg ttttactatc agccgtgaca acagcaagaa taccctctac     240
cttcagatgt cttcactgcg agctgaagac accgctgtgt actattgtgc ccgtcaggac     300
tacggtaact acgtgtggtt cgcttactgg ggacagggaa ccctggtcac cgtctcctcg     360

<210> SEQ ID NO 8
<211> LENGTH: 120
<212> TYPE: PRT
<213> ORGANISM: Artificial Sequence
```

<220> FEATURE:
<223> OTHER INFORMATION: Amino acid sequence of hu67D9 heavy chain
       variable region

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Arg Asp Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Asp Tyr Gly Asn Tyr Val Trp Phe Ala Tyr Trp Gly Gln
            100                 105                 110

Gly Thr Leu Val Thr Val Ser Ser
        115                 120

<210> SEQ ID NO 9
<211> LENGTH: 336
<212> TYPE: DNA
<213> ORGANISM: Artificial Sequence
<220> FEATURE:
<223> OTHER INFORMATION: Nucleotide sequence of hu67D9 light chain
       variable region

<400> SEQUENCE: 9
gatattgttc tgacccagtc ccccgcttca ctggctgtga gtcctgggca gcgagctacc      60
atcagctgcc gggcttcaga gtccgtggat agctacggaa tttcatttat gcactggttc     120
cagcagaagc caggccaacc acctcagttg ctgatatatt cgacatctaa tcggggaagc     180
ggtgtgccag cccggtttag tggtagcggc tctggtacag atttctctct tacaattaac     240
ccagtggagg cggatgacac tgccaattac ttttgtcagc agagccagga agtgccttgg     300
acttttggtc agggcacgaa ggtagagatt aaacgg                              336

<210> SEQ ID NO 10
<211> LENGTH: 112
<212> TYPE: PRT
<213> ORGANISM: Artificial Sequence
<220> FEATURE:
<223> OTHER INFORMATION: Amino acid sequence of hu67D9 light chain
       variable region

<400> SEQUENCE: 10

Asp Ile Val Leu Thr Gln Ser Pro Ala Ser Leu Ala Val Ser Pro Gly
1               5                   10                  15

Gln Arg Ala Thr Ile Ser Cys Arg Ala Ser Glu Ser Val Asp Ser Tyr
            20                  25                  30

Gly Ile Ser Phe Met His Trp Phe Gln Gln Lys Pro Gly Gln Pro Pro
        35                  40                  45

Gln Leu Leu Ile Tyr Ser Thr Ser Asn Arg Gly Ser Gly Val Pro Ala
    50                  55                  60

Arg Phe Ser Gly Ser Gly Ser Gly Thr Asp Phe Ser Leu Thr Ile Asn
65                  70                  75                  80

```
Pro Val Glu Ala Asp Asp Thr Ala Asn Tyr Phe Cys Gln Gln Ser Gln
             85                  90                  95

Glu Val Pro Trp Thr Phe Gly Gln Gly Thr Lys Val Glu Ile Lys Arg
        100                 105                 110
```

<210> SEQ ID NO 11
<211> LENGTH: 1173
<212> TYPE: DNA
<213> ORGANISM: Artificial Sequence
<220> FEATURE:
<223> OTHER INFORMATION: Nucleotide sequence of the DNA containing cDNA
      encoding the extracellular region of human PD-1 fused to human Fc

<400> SEQUENCE: 11

```
aagcttcttg ccgccaccat gcagatccca caggcgccct ggccagtcgt ctgggcggtg      60
ctacaactgg gctggcggcc aggatggttc ttagactccc cagacaggcc ctggaacccc     120
cccaccttct ccccagccct gctcgtggtg accgaagggg acaacgccac cttcacctgc     180
agcttctcca acacatcgga gagcttcgtg ctaaactggt accgcatgag ccccagcaac     240
cagacggaca agctggccgc cttccccgag accgcagcc agcccggcca ggactgccgc     300
ttccgtgtca cacaactgcc caacgggcgt gacttccaca tgagcgtggt cagggcccgg     360
cgcaatgaca gcggcaccta cctctgtggg gccatctccc tggccccaa ggcgcagatc      420 aaagagagcc tgcgggcaga gctcagggtg acagagagaa gggctagcga gcccaaatct     480
tgtgacaaaa ctcacacatg cccaccgtgc ccagcacctg aactcctggg gggaccgtca     540
gtcttcctct tccccccaaa acccaaggac accctcatga tctcccggac ccctgaggtc     600
acatgcgtgg tggtggacgt gagccacgaa gaccctgagg tcaagttcaa ctggtacgtg     660
gacggcgtgg aggtgcataa tgccaagaca aagccgcggg aggagcagta caacagcacg     720
taccgtgtgg tcagcgtcct caccgtcctg caccaggact ggctgaatgg caaggagtac     780
aagtgcaagg tctccaacaa agccctccca gcccccatcg agaaaaccat ctccaaagcc     840
aaagggcagc cccgagaacc acaggtgtac accctgcccc catctcggga ggagatgacc     900
aagaaccagg tcagcctgac ctgcctggtc aaaggcttct atcccagcga catcgccgtg     960
gagtgggaga gcaatgggca gccggagaac aactacaaga ccacgcctcc cgtgctggac    1020
tccgacggct ccttcttcct ctatagcaag ctcaccgtgg acaagagcag gtggcagcag    1080
gggaacgtct tctcatgctc cgtgatgcat gaggctctgc acaaccacta cacgcagaag    1140
agcctctccc tgtccccggg taaatgagaa ttc                                 1173
```

<210> SEQ ID NO 12
<211> LENGTH: 1443
<212> TYPE: DNA
<213> ORGANISM: Artificial Sequence
<220> FEATURE:
<223> OTHER INFORMATION: Nucleotide sequence of the DNA containing cDNA
      encoding the extracellular region of human PD-L1 fused to human Fc

<400> SEQUENCE: 12

```
aagcttgccg ccaccatgag gatatttgct gtctttatat tcatgaccta ctggcatttg      60
ctgaacgcat ttactgtcac ggttcccaag gacctatatg tggtagagta tggtagcaat     120
atgacaattg aatgcaaatt cccagtagaa aaacaattag acctggctgc actaattgtc     180
tattgggaaa tggaggataa gaacattatt caatttgtgc atggagagga agacctgaag     240
gttcagcata gtagctacag acagagggcc cggctgttga aggaccagct ctccctggga     300
aatgctgcac ttcagatcac agatgtgaaa ttgcaggatg caggggtgta ccgctgcatg     360
```

| | |
|---|---|
| atcagctatg gtggtgccga ctacaagcga attactgtga aagtcaatgc cccatacaac | 420 |
| aaaatcaacc aaagaatttt ggttgtggat ccagtcacct ctgaacatga actgacatgt | 480 |
| caggctgagg gctacccccaa ggccgaagtc atctggacaa gcagtgacca tcaagtcctg | 540 |
| agtggtaaga ccaccaccac caattccaag agagaggaga aacttttcaa tgtgaccagc | 600 |
| acactgagaa tcaacacaac aactaatgag attttctact gcacttttag gagattagat | 660 |
| cctgaggaaa accatacagc tgaattggtc atcccagaac tacctctggc acatcctcca | 720 |
| aatgaaagga ctgctagcga gcccaaatct tgtgacaaaa ctcacacatg cccaccgtgc | 780 |
| ccagcacctg aactcctggg gggaccgtca gtcttcctct tccccccaaa acccaaggac | 840 |
| accctcatga tctcccggac ccctgaggtc acatgcgtgg tggtggacgt gagccacgaa | 900 |
| gaccctgagg tcaagttcaa ctggtacgtg acggcgtgg aggtgcataa tgccaagaca | 960 |
| aagccgcggg aggagcagta caacagcacg taccgtgtgg tcagcgtcct caccgtcctg | 1020 |
| caccaggact ggctgaatgg caaggagtac aagtgcaagg tctccaacaa agccctccca | 1080 |
| gcccccatcg agaaaaccat ctccaaagcc aagggcagc cccgagaacc acaggtgtac | 1140 |
| accctgcccc catcccggga tgagctgacc aagaaccagg tcagcctgac ctgcctggtc | 1200 |
| aaaggcttct atcccagcga catcgccgtg gagtgggaga gcaatgggca gccggagaac | 1260 |
| aactacaaga ccacgcctcc cgtgctggac tccgacggct ccttcttcct ctacagcaag | 1320 |
| ctcaccgtgg acaagagcag gtggcagcag gggaacgtct tctcatgctc cgtgatgcat | 1380 |
| gaggctctgc acaaccacta cacgcagaag agcctctccc tgtccccggg taaatgagaa | 1440 |
| ttc | 1443 |

<210> SEQ ID NO 13
<211> LENGTH: 888
<212> TYPE: DNA
<213> ORGANISM: Homo sapiens

<400> SEQUENCE: 13

| | |
|---|---|
| aagcttgccg ccaccatgca gatcccacag gcgccctggc cagtcgtctg ggcggtgcta | 60 |
| caactgggct ggcggccagg atggttctta gactccccag acaggccctg gaaccccccc | 120 |
| accttctccc cagccctgct cgtggtgacc gaaggggaca cgccaccttt cacctgcagc | 180 |
| ttctccaaca tcggagagag cttcgtgcta aactggtacc gcatgagccc cagcaaccag | 240 |
| acggacaagc tggccgcctt ccccgaggac cgcagccagc ccggccagga ctgccgcttc | 300 |
| cgtgtcacac aactgcccaa cgggcgtgac ttcacatga gcgtggtcag ggcccggcgc | 360 |
| aatgacagcg gcacctacct ctgtggggcc atctccctgg cccccaaggc gcagatcaaa | 420 |
| gagagcctgc gggcagagct cagggtgaca gagagaaggg cagaagtgcc cacagcccac | 480 |
| cccagcccct cacccaggcc agccggccag ttccaaaccc tggtggttgg tgtcgtgggc | 540 |
| ggcctgctgg gcagcctggt gctgctagtc tgggtcctgg ccgtcatctg ctcccgggcc | 600 |
| gcacgaggga caataggagc caggcgcacc ggccagcccc tgaaggagga cccctcagcc | 660 |
| gtgcctgtgt tctctgtgga ctatgggag ctggatttcc agtggcgaga gaagaccccg | 720 |
| gagcccccg tgcctgtgt ccctgagcag acggagtatg ccaccattgt ctttcctagc | 780 |
| ggaatgggca cctcatcccc cgcccgcagg ggctcagctg acggccctcg gagtgcccag | 840 |
| ccactgaggc ctgaggatgg acactgctct tggcccctct gagaattc | 888 |

<210> SEQ ID NO 14

<211> LENGTH: 268
<212> TYPE: PRT
<213> ORGANISM: Homo sapiens

<400> SEQUENCE: 14

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
            20                  25                  30
Thr Cys Ser Phe Ser Asn Thr Ser Glu Ser Phe Val Leu Asn Trp Tyr
        35                  40                  45
Arg Met Ser Pro Ser Asn Gln Thr Asp Lys Leu Ala Ala Phe Pro Glu
    50                  55                  60
Asp Arg Ser Gln Pro Gly Gln Asp Cys Arg Phe Arg Val Thr Gln Leu
65                  70                  75                  80
Pro Asn Gly Arg Asp Phe His Met Ser Val Val Arg Ala Arg Arg Asn
                85                  90                  95
Asp Ser Gly Thr Tyr Leu Cys Gly Ala Ile Ser Leu Ala Pro Lys Ala
            100                 105                 110
Gln Ile Lys Glu Ser Leu Arg Ala Glu Leu Arg Val Thr Glu Arg Arg
        115                 120                 125
Ala Glu Val Pro Thr Ala His Pro Ser Pro Ser Pro Arg Pro Ala Gly
    130                 135                 140
Gln Phe Gln Thr Leu Val Val Gly Val Val Gly Gly Leu Leu Gly Ser
145                 150                 155                 160
Leu Val Leu Leu Val Trp Val Leu Ala Val Ile Cys Ser Arg Ala Ala
                165                 170                 175
Arg Gly Thr Ile Gly Ala Arg Arg Thr Gly Gln Pro Leu Lys Glu Asp
            180                 185                 190
Pro Ser Ala Val Pro Val Phe Ser Val Asp Tyr Gly Glu Leu Asp Phe
        195                 200                 205
Gln Trp Arg Glu Lys Thr Pro Glu Pro Pro Val Pro Cys Val Pro Glu
    210                 215                 220
Gln Thr Glu Tyr Ala Thr Ile Val Phe Pro Ser Gly Met Gly Thr Ser
225                 230                 235                 240
Ser Pro Ala Arg Arg Gly Ser Ala Asp Gly Pro Arg Ser Ala Gln Pro
                245                 250                 255
Leu Arg Pro Glu Asp Gly His Cys Ser Trp Pro Leu
            260                 265

<210> SEQ ID NO 15
<211> LENGTH: 360
<212> TYPE: DNA
<213> ORGANISM: Artificial Sequence
<220> FEATURE:
<223> OTHER INFORMATION: Nucleotide sequence of the heavy chain variable
      region of 67D9

<400> SEQUENCE: 15
gaagtgattc tggtggagtc tgggggaggc ttagtgaagc ctggagggtc cctgaaagtc      60
tcctgtgcgg cctctggatt cactttcagt acctatggca tgtcttgggt tcgccagact     120
ccggagaaga ggctggagtg gtcgcaacc attagtggtg gtggtcgtga cacctactat     180
ccagacactg tgaaggggcg attcaccatc tccagagaca tgccaaaaa taccctgtat     240 ctacaaatga gcagtctgag gtctgaggac acggccttgt attattgtgc aagacaggac     300
tatggtaact acgtatggtt tgcttactgg ggccaaggga ctctggtcac tgtctctgca     360

<210> SEQ ID NO 16
<211> LENGTH: 120
<212> TYPE: PRT
<213> ORGANISM: Artificial Sequence
<220> FEATURE:
<223> OTHER INFORMATION: Amino acid sequence of the heavy chain variable
      region of 67D9

<400> SEQUENCE: 16

Glu Val Ile Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Thr Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Arg Asp Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Asp Tyr Gly Asn Tyr Val Trp Phe Ala Tyr Trp Gly Gln
            100                 105                 110

Gly Thr Leu Val Thr Val Ser Ala
        115                 120

<210> SEQ ID NO 17
<211> LENGTH: 336
<212> TYPE: DNA
<213> ORGANISM: Artificial Sequence
<220> FEATURE:
<223> OTHER INFORMATION: Nucleotide sequence of the light chain variable
      region of 67D9

<400> SEQUENCE: 17
gacattgtgc tgacccaatc tccagcttct ttggctgtgt ctctagggca gagggccacc      60
atctcctgca gagccagcga aagtgttgat agttatggca ttagttttat gcactggttc     120
caacagaaac aggacagcc accccaactc ctcatctatt ctacatccaa ccgaggatcc     180
ggggtccctg ccaggtttag tggcagtggg tctgggacag acttcagcct caccatccat     240
cctatggagg aggatgatac tgcaatgtat ttctgtcagc aaagtcagga ggttccgtgg     300
acgttcggtg aggcaccaa gctggaaatc aaacgg                                336

<210> SEQ ID NO 18
<211> LENGTH: 112
<212> TYPE: PRT
<213> ORGANISM: Artificial Sequence
<220> FEATURE:
<223> OTHER INFORMATION: Amino acid sequence of the light chain variable
      region of 67D9

<400> SEQUENCE: 18

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Ile Ser Phe Met His Trp Phe Gln Gln Lys Pro Gly Gln Pro Pro
        35                  40                  45

Gln Leu Leu Ile Tyr Ser Thr Ser Asn Arg Gly Ser Gly Val Pro Ala
         50              55                  60

Arg Phe Ser Gly Ser Gly Ser Gly Thr Asp Phe Ser Leu Thr Ile His
65                  70                  75                  80

Pro Met Glu Glu Asp Asp Thr Ala Met Tyr Phe Cys Gln Gln Ser Gln
                 85                  90                  95

Glu Val Pro Trp Thr Phe Gly Gly Gly Thr Lys Leu Glu Ile Lys Arg
             100                 105                 110

```
<210> SEQ ID NO 19
<211> LENGTH: 1422
<212> TYPE: DNA
<213> ORGANISM: Homo sapiens

<400> SEQUENCE: 19
aagcttgccg ccaccatgaa cttcggactc agcttgattt tccttgtcct aattttaaaa         60
ggtgtccagt gtgaagtgat tctggtggag tctgggggag gcttagtgaa gcctggaggg        120
tccctgaaag tctcctgtgc ggcctctgga ttcactttca gtacctatgg catgtcttgg        180
gttcgccaga ctccggagaa gaggctggag tgggtcgcaa ccattagtgg tggtggtcgt        240
gacacctact atccagacac tgtgaagggg cgattcacca tctccagaga caatgccaaa        300
aataccctgt atctacaaat gagcagtctg aggtctgagg acacggcctt gtattattgt        360
gcaagacagg actatggtaa ctacgtatgg tttgcttact ggggccaagg gactctggtc        420
actgtctctg cagctagcac caagggccca tccgtcttcc ccctggcgcc ctgctccagg        480
agcacctccg agagcacagc cgccctgggc tgcctggtca aggactactt ccccgaaccg        540
gtgacggtgt cgtggaactc aggcgccctg accagcggcg tgcacacctt cccggctgtc        600
ctacagtcct caggactcta ctccctcagc agcgtggtga ccgtgccctc agcagcttg         660
ggcacgaaga cctacacctg caacgtagat cacaagccca gcaacaccaa ggtggacaag        720
agagttgagt ccaaatatgg tcccccatgc ccacccctgcc cagcacctga gttcctgggg        780
ggaccatcag tcttcctgtt ccccccaaaa cccaaggaca ctctcatgat ctcccggacc        840
cctgaggtca cgtgcgtggt ggtggacgtg agccaggaag accccgaggt ccagttcaac        900
tggtacgtgg atggcgtgga ggtgcataat gccaagacaa agccgcggga ggagcagttc        960
aacagcacgt accgtgtggt cagcgtcctc accgtcctgc accaggactg gctgaacggc       1020
aaggagtaca agtgcaaggt ctccaacaaa ggcctcccgt cctccatcga gaaaaccatc       1080
tccaaagcca agggcagccc cgagagccca caggtgtaca ccctgccccc atcccaggag       1140
gagatgacca agaaccaggt cagcctgacc tgcctggtca aaggcttcta ccccagcgac       1200
atcgccgtgg agtgggagag caatgggcag ccggagaaca actacaagac cacgcctccc       1260
gtgctggact ccgacggctc cttcttcctc tacagcaggc taaccgtgga caagagcagg       1320
tggcaggagg ggaatgtctt ctcatgctcc gtgatgcacg aggctctgca caaccactac       1380
acacagaaga gcctctcccct gtctctgggt aaatgagaat tc                          1422

<210> SEQ ID NO 20
<211> LENGTH: 738
<212> TYPE: DNA
<213> ORGANISM: Artificial Sequence
<220> FEATURE:
<223> OTHER INFORMATION: Nucleotide sequence of the DNA containing the
      cDNA encoding the c67D9 light chain

<400> SEQUENCE: 20
```

-continued

```
aagcttgccg ccaccatgga aaagacaca ctcctgctat gggtcctgct tctctgggtt    60
ccaggttcca caggtgacat tgtgctgacc caatctccag cttctttggc tgtgtctcta   120
gggcagaggg ccaccatctc ctgcagagcc agcgaaagtg ttgatagtta tggcattagt   180
tttatgcact ggttccaaca gaaaccagga cagccacccc aactcctcat ctattctaca   240
tccaaccgag atccggggt ccctgccagg tttagtggca gtgggtctgg gacagacttc    300
agcctcacca tccatcctat ggaggaggat gatactgcaa tgtatttctg tcagcaaagt   360
caggaggttc cgtggacgtt cggtggaggc accaagctgg aaatcaaacg gactgtggct   420
gcaccatctg tcttcatctt cccgccatct gatgagcagt tgaaatctgg aactgcctct   480
gttgtgtgcc tgctgaataa cttctatccc agagaggcca agtacagtg gaaggtggat    540
aacgccctcc aatcgggtaa ctcccaggag agtgtcacag agcaggacag caaggacagc   600
acctacagcc tcagcagcac cctgacgctg agcaaagcag actacgagaa acacaaagtc   660
tacgcctgcg aagtcaccca tcagggcctg agctcgcccg tcacaaagag cttcaacagg   720
ggagagtgtt aggaattc                                                 738
```

<210> SEQ ID NO 21
<211> LENGTH: 447
<212> TYPE: PRT
<213> ORGANISM: Artificial Sequence
<220> FEATURE:
<223> OTHER INFORMATION: Amino acid sequence of c67D9 heavy chain

<400> SEQUENCE: 21

```
Glu Val Ile Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Thr Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Arg Asp Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Asp Tyr Gly Asn Tyr Val Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
```

```
            225                 230                 235                 240
        Phe Leu Phe Pro Pro Lys Pro Lys Asp Thr Leu Met Ile Ser Arg Thr
                        245                 250                 255

Pro Glu Val Thr Cys Val Val Asp Val Ser Gln Glu Asp Pro Glu
                        260                 265                 270

Val Gln Phe Asn Trp Tyr Val Asp Gly Val Glu Val His Asn Ala Lys
                        275                 280                 285

Thr Lys Pro Arg Glu Glu Gln Phe Asn Ser Thr Tyr Arg Val Val Ser
                        290                 295                 300

Val Leu Thr Val Leu His Gln Asp Trp Leu Asn Gly Lys Glu Tyr Lys
        305                 310                 315                 320

Cys Lys Val Ser Asn Lys Gly Leu Pro Ser Ser Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Gln Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Arg Leu Thr Val Asp Lys Ser Arg
                        405                 410                 415

Trp Gln Glu Gly Asn Val Phe Ser Cys Ser Val Met His Glu Ala Leu
                        420                 425                 430

His Asn His Tyr Thr Gln Lys Ser Leu Ser Leu Ser Leu Gly Lys
                        435                 440                 445

<210> SEQ ID NO 22
<211> LENGTH: 218
<212> TYPE: PRT
<213> ORGANISM: Artificial Sequence
<220> FEATURE:
<223> OTHER INFORMATION: Amino acid sequence of c67D9 light chain

<400> SEQUENCE: 22

Asp Ile Val Leu Thr Gln Ser Pro Ala Ser Leu Ala Val Ser Leu Gly
        1               5                   10                  15

Gln Arg Ala Thr Ile Ser Cys Arg Ala Ser Glu Ser Val Asp Ser Tyr
                        20                  25                  30

Gly Ile Ser Phe Met His Trp Phe Gln Gln Lys Pro Gly Gln Pro Pro
                        35                  40                  45

Gln Leu Leu Ile Tyr Ser Thr Ser Asn Arg Gly Ser Gly Val Pro Ala
                        50                  55                  60

Arg Phe Ser Gly Ser Gly Ser Gly Thr Asp Phe Ser Leu Thr Ile His
        65                  70                  75                  80

Pro Met Glu Glu Asp Asp Thr Ala Met Tyr Phe Cys Gln Gln Ser Gln
                        85                  90                  95

Glu Val Pro Trp Thr Phe Gly Gly Gly Thr Lys Leu Glu Ile Lys Arg
                        100                 105                 110

Thr Val Ala Ala Pro Ser Val Phe Ile Phe Pro Pro Ser Asp Glu Gln
                        115                 120                 125

Leu Lys Ser Gly Thr Ala Ser Val Val Cys Leu Leu Asn Asn Phe Tyr
                        130                 135                 140

Pro Arg Glu Ala Lys Val Gln Trp Lys Val Asp Asn Ala Leu Gln Ser
```

```
145                 150                 155                 160
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
                210                 215

<210> SEQ ID NO 23
<211> LENGTH: 362
<212> TYPE: PRT
<213> ORGANISM: Artificial Sequence
<220> FEATURE:
<223> OTHER INFORMATION: Amino acid sequences of PD-1-Fc fusion protein

<400> SEQUENCE: 23

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
                35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
                115                 120                 125

Ala Ser Glu Pro Lys Ser Cys Asp Lys Thr His Thr Cys Pro Pro Cys
        130                 135                 140

Pro Ala Pro Glu Leu Leu Gly Gly Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
                180                 185                 190

Tyr Val Asp Gly Val Glu Val His Asn Ala Lys Thr Lys Pro Arg Glu
                195                 200                 205

Glu Gln Tyr Asn Ser Thr Tyr Arg Val Val Ser Val Leu Thr Val Leu
        210                 215                 220

His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Glu Glu
                260                 265                 270

Met Thr Lys Asn Gln Val Ser Leu Thr Cys Leu Val Lys Gly Phe Tyr
                275                 280                 285

Pro Ser Asp Ile Ala Val Glu Trp Glu Ser Asn Gly Gln Pro Glu Asn
```

```
                290                 295                 300
Asn Tyr Lys Thr Thr Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
                340                 345                 350

Gln Lys Ser Leu Ser Leu Ser Pro Gly Lys
        355                 360

<210> SEQ ID NO 24
<211> LENGTH: 455
<212> TYPE: PRT
<213> ORGANISM: Artificial Sequence
<220> FEATURE:
<223> OTHER INFORMATION: Amino acid sequences of PD-L1-Fc fusion protein

<400> SEQUENCE: 24

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Thr Ala Ser Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
```

```
                290                 295                 300
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Asp Glu Leu Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys
    450                 455

<210> SEQ ID NO 25
<211> LENGTH: 1431
<212> TYPE: DNA
<213> ORGANISM: Artificial Sequence
<220> FEATURE:
<223> OTHER INFORMATION: Nucleotide sequence of the DNA containing the
      cDNA encoding the hu67D9 heavy chain

<400> SEQUENCE: 25
aagcttgccg ccaccatgga ttttcaggtg cagattttca gcttcctgct aatcagtgcc      60
tcagtcataa tatccagagg agaggtgcag ctcgtggaat ctgggggcgg actggtgcag     120
cccggtggaa gtctccggct gagctgcgcc gctagtgggt tcacttttc tacttacggg     180 atgtcttggg tccgacaggc accaggcaag ggctgagagt gggtggctac tatttctgga     240
ggaggccgag acacctacta ccccgacacc gtcaagggac gttttactat cagccgtgac     300
aacagcaaga ataccctcta ccttcagatg tcttcactgc gagctgaaga caccgctgtg     360
tactattgtg cccgtcagga ctacggtaac tacgtgtggt tcgcttactg gggacaggga     420
accctggtca ccgtctcctc ggctagcacc aagggcccat ccgtcttccc cctggcgccc     480
tgctccagga gcacctccga gagcacagcc gccctgggct gcctggtcaa ggactacttc     540
cccgaaccgg tgacggtgtc gtggaactca ggcgccctga ccagcggcgt gcacaccttc     600
ccggctgtcc tacagtcctc aggactctac tccctcagca gcgtggtgac cgtgccctcc     660
agcagcttgg gcacgaagac ctacacctgc aacgtagatc acaagcccag caacaccaag     720
gtggacaaga gagttgagtc caaatatggt cccccatgcc caccctgccc agcacctgag     780
ttcctggggg gaccatcagt cttcctgttc cccccaaaac ccaaggacac tctcatgatc     840
tcccggaccc ctgaggtcac gtgcgtggtg gtggacgtga gccaggaaga ccccgaggtc     900
cagttcaact ggtacgtgga tggcgtggag gtgcataatg ccaagacaaa gccgcgggag     960
gagcagttca acagcacgta ccgtgtggtc agcgtcctca ccgtcctgca ccaggactgg    1020
ctgaacggca aggagtacaa gtgcaaggtc tccaacaaag cctcccgtc ctccatcgag     1080
```

```
aaaaccatct ccaaagccaa agggcagccc cgagagccac aggtgtacac cctgccccca    1140
tcccaggagg agatgaccaa gaaccaggtc agcctgacct gcctggtcaa aggcttctac    1200
cccagcgaca tcgccgtgga gtgggagagc aatgggcagc cggagaacaa ctacaagacc    1260
acgcctcccg tgctggactc cgacggctcc ttcttcctct acagcaggct aaccgtggac    1320
aagagcaggt ggcaggaggg gaatgtcttc tcatgctccg tgatgcacga ggctctgcac    1380
aaccactaca cacagaagag cctctccctg tctctgggta aatgagaatt c            1431
```

```
<210> SEQ ID NO 26
<211> LENGTH: 447
<212> TYPE: PRT
<213> ORGANISM: Artificial Sequence
<220> FEATURE:
<223> OTHER INFORMATION: Amino acid sequence of hu67D9 heavy chain

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Arg Asp Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gln Asp Tyr Gly Asn Tyr Val Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly Lys
    435                 440                 445

<210> SEQ ID NO 27
<211> LENGTH: 742
<212> TYPE: DNA
<213> ORGANISM: Artificial Sequence
<220> FEATURE:
<223> OTHER INFORMATION: Nucleotide sequence of the DNA containing the
      cDNA encoding the hu67D9 light chain

<400> SEQUENCE: 27
aagcttgccg ccaccatgga ttttcaggtg cagattttca gcttcctgct aatcagtgcc      60
tcagtcataa tatccagagg agatattgtt ctgacccagt ccccgcttc actggctgtg     120 agtcctgggc agcgagctac catcagctgc cgggcttcag agtccgtgga tagctacgga     180
atttcattta tgcactggtt ccagcagaag ccaggccaac acctcagtt gctgatatat     240 tcgacatcta atcggggaag cggtgtgcca gcccggttta gtggtagcgg ctctggtaca     300
gatttctctc ttacaattaa cccagtggag gcggatgaca ctgccaatta cttttgtcag     360
cagagccagg aagtgccttg acttttggtc agggcacga aggtagagat taaacggact     420
gtggctgcac catctgtctt catcttcccg ccatctgatg agcagttgaa atctggaact     480
gcctctgttg tgtgcctgct gaataacttc tatcccagag aggccaaagt acagtggaag     540
gtggataacg ccctccaatc gggtaactcc caggagagtg tcacagagca ggacagcaag     600
gacagcacct acagcctcag cagcaccctg acgctgagca agcagacta cgagaaacac     660 aaagtctacg cctgcgaagt cacccatcag ggcctgagct cgcccgtcac aaagagcttc     720
aacaggggag agtgttgaat tc                                             742

<210> SEQ ID NO 28
<211> LENGTH: 218
<212> TYPE: PRT
<213> ORGANISM: Artificial Sequence
<220> FEATURE:
<223> OTHER INFORMATION: Amino acid sequence of hu67D9 light chain

<400> SEQUENCE: 28

Asp Ile Val Leu Thr Gln Ser Pro Ala Ser Leu Ala Val Ser Pro Gly
1               5                  10                  15

Gln Arg Ala Thr Ile Ser Cys Arg Ala Ser Glu Ser Val Asp Ser Tyr
            20                  25                  30
```

-continued

```
Gly Ile Ser Phe Met His Trp Phe Gln Gln Lys Pro Gly Gln Pro Pro
        35                  40                  45

Gln Leu Leu Ile Tyr Ser Thr Ser Asn Arg Gly Ser Gly Val Pro Ala
    50                  55                  60

Arg Phe Ser Gly Ser Gly Ser Gly Thr Asp Phe Ser Leu Thr Ile Asn
 65              70                  75                      80

Pro Val Glu Ala Asp Asp Thr Ala Asn Tyr Phe Cys Gln Gln Ser Gln
            85                  90                      95

Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

PD-1 ANTIBODIES AND USES THEREOF

TECHNICAL FIELD

The present invention relates generally to immunotherapy in the treatment of human disease. More specifically, the present invention relates to the use of anti-PD-1 antibodies to treat cancer.

BACKGROUND OF THE INVENTION

An adaptive immune response involves activation, selection, and clonal proliferation of two major classes of lymphocytes termed T cells and B cells. After encountering an antigen, T cells proliferate and differentiate into antigen-specific effector cells, while B cells proliferate and differentiate into antibody-secreting cells.

T cell activation is a multi-step process requiring several signaling events between the T cell and an antigen-presenting cell (APC). For T cell activation to occur, two types of signals must be delivered to a resting T cell. The first type is mediated by the antigen-specific T cell receptor (TcR), and confers specificity to the immune response. The second, costimulatory, type regulates the magnitude of the response and is delivered through accessory receptors on the T cell.

A primary costimulatory signal is delivered through the activating CD28 receptor upon engagement of its ligands B7-1 or B7-2. In contrast, engagement of the inhibitory CTLA-4 receptor by the same B7-1 or B7-2 ligands results in attenuation of T cell response. Thus, CTLA-4 signals antagonize costimulation mediated by CD28. At high antigen concentrations, CD28 costimulation overrides the CTLA-4 inhibitory effect. Temporal regulation of the CD28 and CTLA-4 expression maintains a balance between activating and inhibitory signals and ensures the development of an effective immune response, while safeguarding against the development of autoimmunity.

Molecular homologues of CD28 and CTLA-4 and their B-7 like ligands have been recently identified. ICOS is a CD28-like costimulatory receptor. PD-1 (Programmed Death 1) is an inhibitory member of the CD28 family of receptors, that also include CD28, CTLA-4, ICOS and BTLA. PD-1 is expressed on activated B cells, T cells, and myeloid cells. The initial members of the family, CD28 and ICOS, were discovered by functional effects on augmenting T cell proliferation following the addition of monoclonal antibodies (Hutloff et al. (1999) Nature 397:263-266; Hansen et al. (1980) Immunogenics 10:247-260). PD-1 was discovered through screening for differential expression in apototic cells (Ishida et al. (1992) EMBO J 11:3887-95). The other members of the family, CTLA-4, and BTLA were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members.

The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM). Although structurally similar to CTLA-4, PD-1 lacks the MYPPPY motif that is critical for B7-1 and B7-2 binding. Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-1 is an inhibitory member of the CD28 family expressed on activated B cells, T cells, and myeloid cells. One ligand for PD-1, PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

SUMMARY OF THE INVENTION

The present invention provides monoclonal antibodies that bind to PD-1 and that exhibit numerous desirable properties. These properties include, for example, high affinity binding to human PD-1.

The invention provides an isolated monoclonal antibody, or an antigen-binding fragment thereof, wherein said monoclonal antibody binds to human PD-1 with high affinity. The monoclonal antibody of the present invention is a mouse, chimeric, or humanized antibody. The antigen-binding fragment of this invention is a Fab, Fab', F(ab)$_2$, or F(ab')$_2$.

The present invention also provides isolated nucleic acid molecules, which encode the anti-PD-1 monoclonal antibody.

The present invention also provides expression vectors comprising the nucleic molecule encoding the anti-PD-1 monoclonal antibody.

The present invention also provides host cells comprising the expression vector comprising the nucleic molecule encoding the anti-PD-1 monoclonal antibody.

The present invention also provides methods of modulating immune responses using anti-PD-1 antibodies. In particular, the invention provides a method of inhibiting growth of tumor cells using anti-PD-1 antibodies.

In one aspect, there is provided an anti-PD-1 monoclonal antibody or an antigen-binding fragment thereof, wherein said antibody comprises a heavy chain variable region comprising SEQ ID NO: 1 (heavy chain CDR1), SEQ ID NO: 2 (heavy chain CDR2), SEQ ID NO: 3 (heavy chain CDR3) and a light chain variable region comprising SEQ ID NO: 4 (light chain CDR1), SEQ ID NO: 5 (light chain CDR2) and SEQ ID NO: 6 (light chain CDR3).

In another aspect, there is provided a composition comprising the monoclonal antibody or antigen-binding fragment thereof as described herein and a pharmaceutically acceptable carrier.

In another aspect, there is provided an immunoconjugate comprising the monoclonal antibody or antigen-binding fragment thereof as described herein linked to a therapeutic agent.

In another aspect, there is provided a method of modulating an immune response in a subject comprising administering to the subject the antibody, or antigen-binding portion thereof, as described herein such that the immune response in the subject is modulated.

In another aspect, there is provided a method of inhibiting growth of tumor cells in a subject, comprising administering to a subject the antibody, or antigen-binding fragment thereof, as described herein in an amount effective to inhibit growth of the tumor cells.

In another aspect, there is provided a method of treating an infectious disease in a subject comprising administering to the subject the antibody, or antigen-binding fragment thereof as described herein such that the subject is treated for the infectious disease.

BRIEF DESCRIPTION OF THE DRAWINGS

The invention will be better understood with reference to the detailed description when considered in conjunction with the non-limiting examples and the accompanying drawings, in which:

FIGS. 1A and 1B show the binding of PD-L1-Fc to PD-1-transfected CHO cells (CHO/PD-1).

FIG. 3 shows amino acid sequences of heavy (A) and light (B) chain variable regions of 67D9 and hu67D9. 67D9VH and 67D9VL indicate heavy and light chain variable regions of 67D9, respectively. The humIII was chosen as framework for the humanized heavy chains and the humκIII was chosen for the humanized light chains. hu67D9VH and hu67D9VL indicate heavy and light chain variable regions of hu67D9, respectively. The dashes represent amino acids that are the same as the corresponding residues in human antibody framework. The CDRs are enclosed with brackets.

FIG. 4A-4D show the results of experiments demonstrating that all of the three anti-PD-1 antibodies, 67D9, c67D9, and hu67D9, effectively inhibit the binding of PD-L1-Fc to PD-1 expressed on transfected CHO-K1 cells.

FIGS. 5A-5D show the results of experiments demonstrating that each of the anti-PD-1 antibodies 67D9 (mouse Ab), c67D9 (chimeric Ab), and hu67D9 (humanized Ab) binds to PD-I (A), but not to ICOS (B), CTLA-4 (C) and CD28(D).

FIGS. 6A-6C show the results of experiments demonstrating that each of the three anti-PD-1 antibodies, 67D9 (mouse Ab), c67D9 (chimeric Ab), and hu67D9 (humanized Ab), promote T-cell proliferation (A), IL-2 (B) secretion and IFN-gamma (C) secretion in a mixed lymphocyte reaction assay.

FIG. 9 shows kinetics and affinity measurement results of Nivolumab and hu67D9.

DETAILED DESCRIPTION OF THE PRESENT INVENTION

Figure 2:
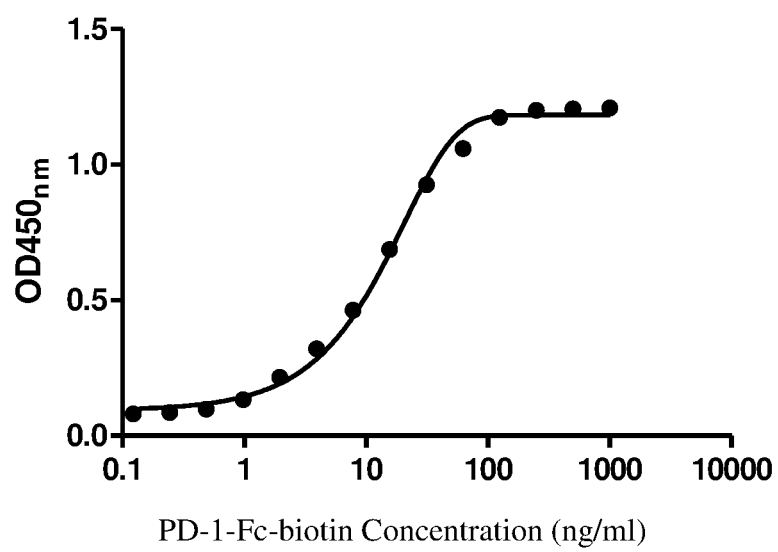
FIG. 2 shows the binding of PD-1-Fc-biotin to PD-L1-Fc.

The present invention relates to isolated monoclonal antibodies, or antigen-binding fragments thereof, which bind specifically to human PD-1. In certain embodiments, the antibodies of the invention exhibit one or more desirable functional properties, such as high affinity binding to PD-1, lack of cross-reactivity to other CD28 family members, the ability to stimulate T cell proliferation and IL-2 and IFN-gamma secretion in mixed lymphocyte reactions, the ability to inhibit binding of one or more PD-1 ligands (e.g., PD-L1 and/or PD-L2), and/or the ability to cross-react with cynomolgus monkey PD-1. In another aspect, the invention relates to the combined use of monoclonal antibodies that bind specifically to PD-1 and monoclonal antibodies that bind specifically to CTLA-4.

The invention provides isolated monoclonal antibodies, or antigen-binding fragments thereof, which bind specifically to human PD-1, and methods of making such antibodies.

In another aspect, the invention pertains to methods of inhibiting growth of tumor cells in a subject using anti-PD-1 antibodies. As demonstrated herein, anti-PD-1 antibodies are capable of inhibiting tumor cell growth in vivo. The invention also relates to methods of using the antibodies to modify an immune response, as well as to treat diseases such as cancer or infectious disease.

In order that the present invention may be more readily understood, certain terms are first defined. Additional definitions are set forth throughout the detailed description.

The terms "Programmed Death 1," "Programmed Cell Death 1," "PD-1," PD1," "PDCD1," "hPD-1" and "hPD-I" are used interchangeably, and include variants, isoforms, species homologs of human PD-1, and analogs having at least one common epitope with PD-1.

The terms "cytotoxic T lymphocyte-associated antigen-4," "CTLA-4," "CTLA4," "CTLA-4 antigen" and "CD152" are used interchangeably, and include variants, isoforms, species homologs of human CTLA-4, and analogs having at least one common epitope with CTLA-4.

The term "immune response" refers to the action of, for example, lymphocytes, antigen presenting cells, phagocytic cells, granulocytes, and soluble macromolecules produced by the above cells or the liver (including antibodies, cytokines, and complements) that results in selective damage to, destruction of, or elimination from the human body of invading pathogens, cells or tissues infected with pathogens, cancerous cells, or, in cases of autoimmunity or pathological inflammation, normal human cells or tissues.

The term "antibody" as referred to herein includes whole antibodies and any antigen-binding fragment (i.e., "antigen-binding portion") or single chains thereof. An "antibody" refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding fragment" of an antibody, as used herein, refers to one or more fragments of an antibody that retain the ability to specifically bind to an antigen (e.g., PD-1). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows chickens, amphibians, reptiles, etc. Except when noted, the terms "patient" or "subject" are used interchangeably.

Various aspects of the invention are described in further detail in the following subsections.

Anti-PD-1 Antibodies

The antibodies of the invention are characterized by particular functional features or properties of the antibodies. For example, the antibodies bind specifically to PD-1 (e.g., bind to human PD-1 and may cross-react with PD-1 from other species, such as cynomolgus monkey). Preferably, an antibody of the invention binds to PD-1 with high affinity, for example with a $K_D$ of $1 \times 10^{-7}$ M or less. The anti-PD-1 antibodies of the invention preferably exhibit one or more of the following characteristics:
(a) does not substantially bind to human CD28, CTLA-4 or ICOS;
(b) increases T-cell proliferation in a Mixed Lymphocyte Reaction (MLR) assay;
(c) increases IFN-γ and/or IL-2 secretion in an MLR assay;
(d) binds to human PD-1 and cynomolgus monkey PD-1;
(e) inhibits the binding of PD-L1 to PD-1;
(f) binds to human PD-1 with a $K_D$ of $1 \times 10^{-7}$ M or less, Preferably, the antibody binds to human PD-1 with a $K_D$ of $1 \times 10^{-8}$ M or less, binds to human PD-1 with a $K_D$ of $5 \times 10^{-9}$ M or less, or binds to human PD-1 with a $K_D$ of between $1 \times 10^{-8}$ M and $1 \times 10^{-12}$ M or less. More preferably, the antibody binds to human PD-1 with a $K_D$ of $1 \times 10^{-12}$ M or less. More preferably, the antibody binds to human PD-1 with a $K_D$ of $3.209 \times 10^{-12}$ M.

An antibody of the invention may exhibit any combination of the above-listed features, such as two, three, four, five or more of the above-listed features.

Standard assays to evaluate the binding ability of the antibodies toward PD-1 are known in the art, including for example, ELISAs, Western blots and RIAs. The binding kinetics (e.g., binding affinity) of the antibodies also can be assessed by standard assays known in the art, such as by Biacore analysis. Suitable assays for evaluating any of the above-described characteristics are described in detail in the Examples.

In one aspect, the invention provides an isolated monoclonal antibody, or antigen-binding fragment thereof, comprising:
(a) a heavy chain variable region comprising SEQ ID NO: 1 (heavy chain CDR1), SEQ ID NO: 2 (heavy chain CDR2), SEQ ID NO: 3 (heavy chain CDR3); and
(b) a light chain variable region comprising SEQ ID NO: 4 (light chain CDR1), SEQ ID NO: 5 (light chain CDR2) and SEQ ID NO: 6 (light chain CDR3);
wherein the antibody specifically binds PD-1, preferably human PD-1.

Preferred the anti-PD-1 antibody includes:
(a) a heavy chain variable region comprising the amino acid sequence of SEQ ID NO:8 or SEQ ID NO:16; and
(b) a light chain variable region comprising the amino acid sequence of SEQ ID NO:10 or SEQ ID NO:18.

Homologous Antibodies

An antibody of the invention comprises heavy and light chain variable regions comprising amino acid sequences that are homologous to the amino acid sequences of the preferred antibodies described herein, and wherein the antibodies retain the desired functional properties of the anti-PD-1 antibodies of the invention.

For example, the invention provides an isolated monoclonal antibody, or antigen-binding portion thereof, comprising a heavy chain variable region and a light chain variable region, wherein:
(a) the heavy chain variable region comprises an amino acid sequence that is at least 80% homologous to an amino acid sequence selected from the group consisting of SEQ ID NOs: 8 and 16;
(b) the light chain variable region comprises an amino acid sequence that is at least 80% homologous to an amino acid sequence selected from the group consisting of SEQ ID NOs: 10, and 18; and the antibody exhibits one or more of the following properties:
(c) does not substantially bind to human CD28, CTLA-4 or ICOS;
(d) increases T-cell proliferation in a Mixed Lymphocyte Reaction (MLR) assay;
(e) increases IFN-γ and/or IL-2 secretion in an MLR assay;
(f) binds to human PD-1 and cynomolgus monkey PD-1;
(g) inhibits the binding of PD-L1 to PD-1;
(h) binds to human PD-1 with a $K_D$ of $1\times10^{-7}$ M or less.

In other embodiments, the $V_H$ and/or $V_L$ amino acid sequences may be 85%, 90%, 95%, 96%, 97%, 98% or 99% homologous to the sequences set forth above.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Immunoconjugates

In another aspect, the present invention features an anti-PD-1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof.

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine[131], indium[111], yttrium[90] and lutetium[177]. Method for preparing radioimmunconjugates are established in the art. Examples of radioimmunoconjugates are commercially available, including Zevalin™. (IDEC Pharmaceuticals) and Bexxar™. (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-PD-1 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline metals or alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-PD-1 antibody of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising an anti-PD-1 antibody and an anti-CTLA-4 antibody, as described herein. The kit may also further comprise instructions for use in the treatment of a hyperproliferative disease (such as cancer as described herein). In another embodiment, the anti-PD-1 and anti-CTLA-4 antibodies may be co-packaged in unit dosage form.

In certain embodiments, two or more monoclonal antibodies with different binding specificities (e.g., anti-PD-1 and anti-CTLA-4) are administered simultaneously, in which case the dosage of each antibody administered falls within the ranges indicated. Antibody can be administered as a single dose or more commonly can be administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art.

Uses and Methods of the Invention

The antibodies, antibody compositions and methods of the present invention have numerous in vitro and in vivo utilities involving, for example, detection of PD-1 or enhancement of immune response by blockade of PD-1. In a preferred embodiment, the antibodies of the present invention are human antibodies. For example, these molecules can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the anti-PD-1 antibodies can be administered together with an antigen of interest. When antibodies to PD-1 are administered together with another agent, the two can be administered in either order or simultaneously.

The invention further provides methods for detecting the presence of human PD-1 antigen in a sample, or measuring the amount of human PD-1 antigen, comprising contacting the sample, and a control sample, with a human monoclonal antibody, or an antigen-binding portion thereof, which specifically binds to human PD-1, under conditions that allow for formation of a complex between the antibody or portion thereof and human PD-1. The formation of a complex is then detected, wherein a difference complex formation between the sample compared to the control sample is indicative the presence of human PD-1 antigen in the sample.

Given the specific binding of the antibodies of the invention for PD-1, compared to CD28, ICOS and CTLA-4, the antibodies of the invention can be used to specifically detect PD-1 expression on the surface of cells and, moreover, can be used to purify PD-1 via immunoaffinity purification.

In another aspect, the invention provides the use of the antibody, or antigen-binding portion thereof, as disclosed herein in the manufacture of a medicament for modifying an immune response in a subject.

Cancer

Blockade of PD-1 by antibodies can enhance the immune response to cancerous cells in the patient. The ligand for PD-1, PD-L1, is not expressed in normal human cells, but is abundant in a variety of human cancers (Dong et al. (2002) Nat Med 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J Mol Med 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 to PD-L1 and the effect is additive when the interaction of PD-1 to PD-L2 is blocked as well. While previous studies have shown that T-cell proliferation can be restored by inhibiting the interaction of PD-1 to PD-L1, there have been no reports of a direct effect on cancer tumor growth in vivo by blocking the PD-1/PD-L1 interaction. In one aspect, the present invention relates to treatment of a subject in vivo using an anti-PD-1 antibody such that growth of cancerous tumors is inhibited. An anti-PD-1 antibody may be used alone to inhibit the growth of cancerous tumors. Alternatively, an anti-PD-1 antibody may be used in conjunction with other immunogenic agents, standard cancer treatments, or other antibodies, as described below.

Accordingly, in one embodiment, the invention provides a method of inhibiting growth of tumor cells in a subject, comprising administering to the subject a therapeutically effective amount of an anti-PD-1 antibody, or antigen-binding portion thereof.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention.

Examples of other cancers that may be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) Int. Immunol. 17:133-144).

Optionally, antibodies to PD-1 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

In humans, some tumors have been shown to be immunogenic such as melanomas. It is anticipated that by raising the threshold of T cell activation by PD-1 blockade, we may expect to activate tumor responses in the host.

Other antibodies which may be used to activate host immune responsiveness can be used in combination with anti-PD-1. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with PD-1 antibodies (Ito, N. et al. (2000) Immunobiology 201 (5) 527-40). Activating antibodies to T cell costimulatory molecules such as CTLA-4, OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

In another embodiment, the invention provides the use of a therapeutically effective amount of an anti-PD-1 antibody, or antigen-binding portion thereof, as disclosed herein in the manufacture of a medicament for inhibiting growth of tumor cells in a subject.

Infectious Diseases

Other methods of the invention are used to treat patients that have been exposed to particular toxins or pathogens. Accordingly, another aspect of the invention provides a method of treating an infectious disease in a subject comprising administering to the subject an anti-PD-1 antibody, or antigen-binding portion thereof, such that the subject is treated for the infectious disease.

Antibody mediated PD-1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, *Giardia*, Malaria, *Leishmania, Staphylococcus aureus, Pseudomonas Aeruginosa*. PD-1 blockade is particularly useful against established infections by agents such as HIV that present altered antigens over the course of the infections. These novel epitopes are recognized as foreign at the time of anti-human PD-1 administration, thus provoking a strong T cell response that is not dampened by negative signals through PD-1.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and conococci, klebsiella, proteus, serratia, pseudomonas, legionella, diphtheria, *salmonella*, bacilli, cholera, tetanus, botulism, anthrax, plague, leptospirosis, and Lymes disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

In all of the above methods, PD-1 blockade can be combined with other forms of immunotherapy such as cytokine treatment (e.g., interferons, GM-CSF, G-CSF, IL-2), or bispecific antibody therapy, which provides for enhanced presentation of tumor antigens.

Another embodiment of the invention provides the use of an anti-PD-1 antibody, or antigen-binding portion thereof, as disclosed herein in the manufacture of a medicament for treating an infectious disease in a subject.

Kits of the Invention

In another aspect, the instant disclosure provides a kit comprising an anti-PD-1 antibody, or antigen-binding portion thereof, as disclosed herein. The kit may also further comprise instructions for use. In another aspect, the kit may be used in any one of the methods or uses as described herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Examples are provided below further illustrating different features of the present invention. The examples also illustrate useful methodology for practicing the invention. These examples do not limit the claimed invention.

Example 1. Construction and Expression of PD-1-Fc and PD-L1-Fc

The DNA (SEQ ID NO.11) containing the cDNA encoding the extracellular region of human PD-1 fused to human Fc was synthesized, with a Hind III site at its 5' end and an EcoRI site at its 3' end. The DNA was digested with Hind III and EcoRI and then was cloned into the pcDNA3.1 (+) vector (Invitrogen), which had been digested with the same restriction enzymes, yielding the expression vector pcDNA3.1(+)-PD-1-Fc. Appropriate pcDNA3.1(+)-PD-1-Fc expression vector was transfected into CHO-K1 cells (ATCC) using Lipofectamine 2000 reagent (Invitrogen). Stable transfectants were isolated by limiting dilution in the presence of 500 µg/ml G418. The clones producing the highest amount of PD-1-Fc protein were selected and grown in serum-free medium. Finally, the PD-1-Fc protein was purified by Protein A affinity chromatography from the serum-free culture supernatant. Protein concentration was determined by absorbance at 280 nm. The amino acid sequence of the PD-1-Fc fusion protein was shown in SEQ ID NO:23.

The DNA (SEQ ID NO.12) containing the cDNA encoding the extracellular region of human PD-L1 fused to human Fc was synthesized, with a Hind III site at its 5' end and an EcoRI site at its 3' end. The DNA was digested with Hind III and EcoRI and then was cloned into the pcDNA3.1 (+) vector (Invitrogen), which had been digested with the same restriction enzymes, yielding the expression vector pcDNA3.1(+)-PD-L1-Fc. Appropriate pcDNA3.1(+)-PD-L1-Fc expression vector was transfected into CHO-K1 cells (ATCC) using Lipofectamine 2000 reagent (Invitrogen). Stable transfectants were isolated by limiting dilution in the presence of 500 μg/ml G418. The clones producing the highest amount of PD-L1-Fc protein were selected and grown in serum-free medium. Finally, the PD-L1-Fc protein was purified by Protein A affinity chromatography from the serum-free culture supernatant. Protein concentration was determined by absorbance at 280 nm. The amino acid sequence of PD-L1-Fc fusion protein was shown in SEQ ID NO: 24.

Example 2. Characterization of PD-L1-Fc Binding to PD-1 Expressed on CHO Cells Chinese hamster ovary (CHO) cell lines that express recombinant human PD-1 at the cell surface were developed and used to determine the binding of PD-L1 to PD-1 by flow cytometry. The DNA (SEQ ID NO.13) containing the cDNA encoding the full-length human PD-1 was synthesized, with a Hind III site at its 5' end and an EcoRI site at its 3' end. The DNA was digested with Hind III and EcoRI and then was cloned into the pcDNA3.1 (+) vector (Invitrogen), which had been digested with the same restriction enzymes, yielding the expression vector pcDNA3.1(+)-PD-1. Appropriate pcDNA3.1(+)-PD-1 expression vector was transfected into CHO-K1 cells (ATCC) using Lipofectamine 2000 reagent (Invitrogen). Stable transfectants were isolated by limiting dilution in the presence of 500 μg/ml G418. The amino acid sequences of the full-length human PD-1 was shown in SEQ ID NO: 14. PD-L1-Fc recombinant protein was labeled with biotin using the biotin protein labeling kit (Roche). Binding of PD-L1 to PD-1 was assessed by incubating the PD-1-transfected CHO cells (CHO/PD-1) with different concentrations of biotin-labeled PD-L1-Fc (biotin-PD-L1-Fc). The cells were washed and binding of was detected with Avidin-FITC. Flow cytometric analyses were performed using a FACScan flow cytometry (Becton Dickinson). The results shown in FIGS. 1A and 1B indicated that biotin-PD-L1-Fc was able to effectively bind CHO/PD-1 cells.

Example 3. Characterization of PD-1-Fc Binding to PD-L1-Fc

PD-1-Fc recombinant protein was labeled with biotin using the biotin protein labeling kit (Roche). Different concentrations of biotin-labeled PD-1-Fc (PD-1-Fc-biotin) were added to 96-well plates coated with PD-L1-Fc, followed by incubation at room temperature for 1 h. After washing, Avidin-HRP was added and the plates were further incubated for 1 h. Finally, 3,3',5,5'-Tetramethylbenzidine (TMB) was added as a substrate for horseradish peroxidase (HRP), and the absorbance was measured at 450 nm. The results shown in FIG. 2 indicated that biotin-PD-1-Fc was able to effectively bind PD-L1-Fc.

Example 4. Generation of Monoclonal Antibodies Against PD-1

To generate monoclonal antibodies to PD-1, 6-week-old female BALB/c mice were immunized three times subcutaneously with the recombinant PD-1-Fc protein in complete Freund's adjuvant (Sigma-Aldrich). Four days after the final booster, the mice were sacrificed and the splenocytes were fused with the SP2/0 cells. The fused cells were suspended in hypoxanthine/aminopterin/thymidine (HAT) selective medium and plated into 96-well microliter plates. After 12 days, the anti-PD-1 antibody-producing hybridoma clones were selected for specifically binding to human PD-1. One hybridoma cell line, which secreted mAbs recognizing human PD-1, was established and named 67D9. The 67D9 antibody isotype was determined to be (IgG2a, κ) with a mouse Ab isotyping kit (Sigma). Finally, the 67D9 antibody was purified by Protein G affinity chromatograph from hybridoma cell culture supernatants.

Example 5. Cloning of 67D9 Heavy and Light Chain Variable Region Genes

RNA was isolated from 67D9 hybridoma cells with TRIzolReagent (Invitrogen). The variable region cDNAs for the light and heavy chains of 67D9 were cloned from the hybridoma cells by 5'RACE system (Invitrogen) according to the manufacturer's instructions. The gene-specific primers (GSPs) for PCR amplification of 67D9 heavy chain were as follows: GSP1-H, 5'-AGC TGG GAA GGT GTG CAC ACC ACT-3'; GSP2-H, 5'-CAG AGT TCC AGG TCA AGG TCA-3'; GSP3-H, 5'-CTT GAC CAG GCA TCC TAG AGT-3'. The GSPs used for PCR amplification of light chain variable regions of 67D9 were as follows: GSP1-L, 5'-TTG CTG TCC TGA TCA GTC CAA CT-3'; GSP2-L, 5'-TGT CGT TCA CTG CCA TCA ATC TT-3'; GSP3-L, 5'-TTG TTC AAG AAG CAC ACG ACT GA-3'. The final PCR products were cloned into pGEM-T vector (Promega) for sequence determination. The nucleotide and amino acid sequences of the heavy chain variable region of 67D9 are shown in SEQ ID NO: 15 and 16, respectively. The nucleotide and amino acid sequences of the light chain variable region of 67D9 are shown in SEQ ID NO: 17 and 18, respectively.

Example 6. Construction and Expression of 67D9 Chimeric Antibody

The DNA (SEQ ID NO.19) containing the cDNA encoding the 67D9 chimeric antibody (c67D9) heavy chain was synthesized, with a Hind III site at its 5' end and an EcoRI site at its 3' end. The DNA was digested with Hind III and EcoRI and then was cloned into the pcDNA3.1 (+) vector (Invitrogen), which had been digested with the same restriction enzymes, yielding the expression vector pcDNA3.1(+)-c67D9H. The DNA (SEQ ID NO.20) containing the cDNA encoding the c67D9 light chain was synthesized, with a Hind III site at its 5' end and an EcoRI site at its 3' end. The DNA was digested with Hind III and EcoRI and then was cloned into the pcDNA3.1 (+) vector (Invitrogen), which had been digested with the same restriction enzymes, yielding the expression vector pcDNA3.1(+)-c67D9L. Appropriate pcDNA3.1(+)-c67D9H and pcDNA3.1(+)-c67D9L expression vectors were co-transfected into CHO-K1 cells using Lipofectamine 2000 reagent. Stable transfectants were isolated by limiting dilution in the presence of 500 μg/ml G418. The clones producing the highest amount of c67D9 were selected and grown in serum-free medium. Finally, c67D9 was purified by Protein A affinity chromatography from the serum-free culture supernatant. Antibody concentration was determined by absorbance at 280 nm. The amino acid sequence of c67D9 heavy chain was shown in SEQ ID NO.21 and the amino acid sequence of c67D9 light chain was shown in SEQ ID NO.22.

Example 7. Humanization of Anti-PD-1 Monoclonal Antibody 67D9

The Protein Data Bank (PDB) was searched for antibody sequences that had high sequence identity with variable fragment (Fv) of 67D9. Two separate BLASTP searches were performed for light chain variable region (VL) and heavy chain variable region (VH) of 67D9. The antibody 1HOD (PDB No. 1HOD) shows 83% identity with the VH of 67D9 and 90% identity with the VL of 67D9. We selected 1HOD as the templates of the VH and VL of 67D9. To construct the three dimensional structure of the 67D9 Fv by homology modeling (INSIGHT II 2003, Accelrys, San Diego, Calif.), the sequences of VL and VH of 67D9 and their templates were aligned, respectively. The coordinates for the structurally conserved regions were assigned from the template and the loop regions were generated by Homology program of Insight II. The new built structure was subjected to molecular dynamics simulations and then energy-minimized by 1000 steps of the steepest descent method and followed by conjugate gradient method using Discover program. Finally, the molecular model of the variable regions of 67D9 was obtained by Insight II molecular modeling software.

The human consensus sequences of light chain subgroup kappa III (humκIII) and heavy chain subgroup III (humIII) were chosen as human framework for the heavy and light chains of humanized version of 67D9, respectively (FIG. 3). The complementarity-determining regions (CDRs) in the humanized antibody were chosen to be identical to those in the mouse antibody 67D9. The molecular model of the 67D9 Fv showed that eight framework region (FR) residues which differed between 67D9 and the human antibody template, were within 5 Å of the CDRs and probably affected the structure of the CDRs. Therefore, these eight FR residues in the humanized 67D9 antibody (hu67D9) were chosen to be the murine 67D9 residues rather than the human antibody residues (FIG. 3). The nucleotide and amino acid sequences of hu67D9 heavy chain variable region were shown in SEQ ID NO. 7 and SEQ ID NO.8, respectively. The nucleotide and amino acid sequences of hu67D9 light chain variable region were shown in SEQ ID NO. 9 and SEQ ID NO.10, respectively.

Example 8. Expression of Anti-PD-1 Humanized Antibody hu67D9

The DNA (SEQ ID NO.25) containing the cDNA encoding the hu67D9 heavy chain was synthesized, with a Hind III site at its 5' end and an EcoRI site at its 3' end. The DNA was digested with Hind III and EcoRI and then was cloned into the pcDNA3.1 (+) vector (Invitrogen), which had been digested with the same restriction enzymes, yielding the expression vector pcDNA3.1(+)-hu67D9H. The DNA (SEQ ID NO.27) containing the cDNA encoding the hu67D9 light chain was synthesized, with a Hind III site at its 5' end and an EcoRI site at its 3' end. The DNA was digested with Hind III and EcoRI and then was cloned into the pcDNA3.1 (+) vector (Invitrogen), which had been digested with the same restriction enzymes, yielding the expression vector pcDNA3.1(+)-hu67D9L. Appropriate pcDNA3.1(+)-hu67D9H and pcDNA3.1(+)-hu67D9L expression vectors were co-transfected into CHO-K1 cells using Lipofectamine 2000 reagent. Stable transfectants were isolated by limiting dilution in the presence of 500 μg/ml G418. The clones producing the highest amount of hu67D9 were selected and grown in serum-free medium. Finally, hu67D9 was purified by Protein A affinity chromatography from the serum-free culture supernatant. Antibody concentration was determined by absorbance at 280 nm. The amino acid sequence of hu67D9 heavy chain was shown in SEQ ID NO.26 and the amino acid sequence of hu67D9 light chain was shown in SEQ ID NO.28.

Example 9. Binding Affinity Measurement

Binding affinities of 67D9, c67D9, and hu67D9 were determined using a similar method described by Holash and colleagues (Holash J, et al. Proc Natl Acad Sci USA. 2002; 99(17):11393-8). Briefly, a fixed concentration of anti-PD-1 antibody was incubated with different concentrations of PD-1-Fc for 1 hour. Then the mixture was added to 96-well plates coated with PD-1-Fc, followed by incubation for 1 h. After washing, HRP-conjugated goat anti-human kappa (for detecting c67D9 or hu67D9) or HRP-conjugated goat anti-mouse kappa (for detecting 67D9) was added and the plates were further incubated for 1 h. Finally, TMB was added as a substrate for HRP, and the absorbance was measured at 450 nm. Our results indicated that the binding affinities (KD) of 67D9, c67D9, and hu67D9 were 12.4 pM, 16.9 pM and 15.4 pM, respectively.

Example 10. Blocking of PD-L1 Binding to PD-1-Expressing CHO-K1 Cells by Anti-PD-1 Antibodies Anti-PD-1 antibodies 67D9, c67D9, and hu67D9 were tested for the ability to block binding of PD-L1 to PD-1 expressed on transfected CHO-K1 (CHO/PD-1) cells by using a flow cytometry assay. Briefly, a subsaturating concentration of biotin-PD-L1-Fc was incubated with 10 μg/ml of 67D9, c67D9, or hu67D9 for 1 hour. Then the mixture was added to the CHO/PD-1 cells. After 1 hour, the cells were washed and binding of was detected with Avidin-PE. Flow cytometric analysis was performed using a FACScan flow cytometry (Becton Dickinson). The results shown in FIG. 4A-4D indicated that all of the three anti-PD-1 antibodies, 67D9, c67D9, and hu67D9, effectively inhibited the binding of PD-L1-Fc to PD-1 expressed on transfected CHO-K1 cells.

Example 11. The Binding of Anti-PD-1 Antibodies to CD28 Family Members

The specificity of anti-PD-1 antibodies was examined by detecting their binding to CD28 family members ICOS, CTLA-4 and CD28 (R&D System) using standard ELISA. Briefly, different concentrations of 67D9, c67D9, or hu67D9 were added to 96-well plates coated with ICOS, CTLA-4, CD28 or PD-1-Fc, followed by incubation at room temperature for 2 h. After washing, HRP-conjugated goat anti-human kappa (for detecting c67D9 or hu67D9) or HRP-conjugated goat anti-mouse kappa (for detecting 67D9) was added and the plates were further incubated for 1 h. Finally, TMB was added as a substrate for HRP, and the absorbance was measured at 450 nm. As shown in FIG. 5A-5D, each of the anti-PD-1 antibodies 67D9, c67D9, and hu67D9 bound to PD-I, but not to the other CD28 family members (ICOS, CTLA-4 and CD28).

Example 12. Effect of Anti-PD-1 Antibodies on Cell Proliferation and Cytokine Production in a Mixed Lymphocyte Reaction A mixed lymphocyte reaction was used to demonstrate the effect of blocking the PD-1 pathway to lymphocyte effector cells. T cells in the assay were tested for proliferation, IFN-gamma secretion and IL-2 secretion in the presence or absence of anti-PD-1 antibodies. Briefly, human peripheral blood mononuclear cells (PBMCs) were isolated from heparinized blood of healthy volunteers by Ficoll-Hypaque density gradient centrifugation. Human PBMCs were cultured in 96-well flat bottom plates overnight. Anti-PD-1 antibodies (67D9, c67D9, or hu67D9) at different antibody concentrations, PMA (10 ng/ml), and ionomycin (10 ng/ml) were added to each culture. A control IgG4 antibody was used as a negative control. The cells were cultured for 3 days at 37° C. Then the cells were labeled with $^3$H-thymidine, cultured for another 6 hours, and analyzed for cell proliferation by using a MicroBeta counter (PerkinElmer). The results shown in FIG. 6A indicated that each of the three anti-PD-1 antibodies, 67D9, c67D9, and hu67D9, promoted T-cell proliferation in a concentration dependent manner.

Human PBMCs were cultured in 96-well flat bottom plates overnight. Anti-PD-1 antibodies (67D9, c67D9, or hu67D9) at different antibody concentrations, PMA (10 ng/ml), and ionomycin (10 ng/ml) were added to each culture. A control IgG4 antibody was used as a negative control. The cells were cultured for 3 days at 37° C. Then 100 µl of medium was taken from each culture for cytokine measurement. The levels of IFN-gamma and IL-2 were measured using ELISA kits (R&D System). The results indicated that each of the three anti-PD-1 antibodies, 67D9, c67D9, and hu67D9, promoted IL-2 (FIG. 6B) and IFN-gamma (FIG. 6C) secretion in a concentration dependent manner.

Example 13. Characterization of Anti-PD-1 Antibody Binding to Mouse PD-1 and Cynomolgus Monkey PD-1

Figure 7:
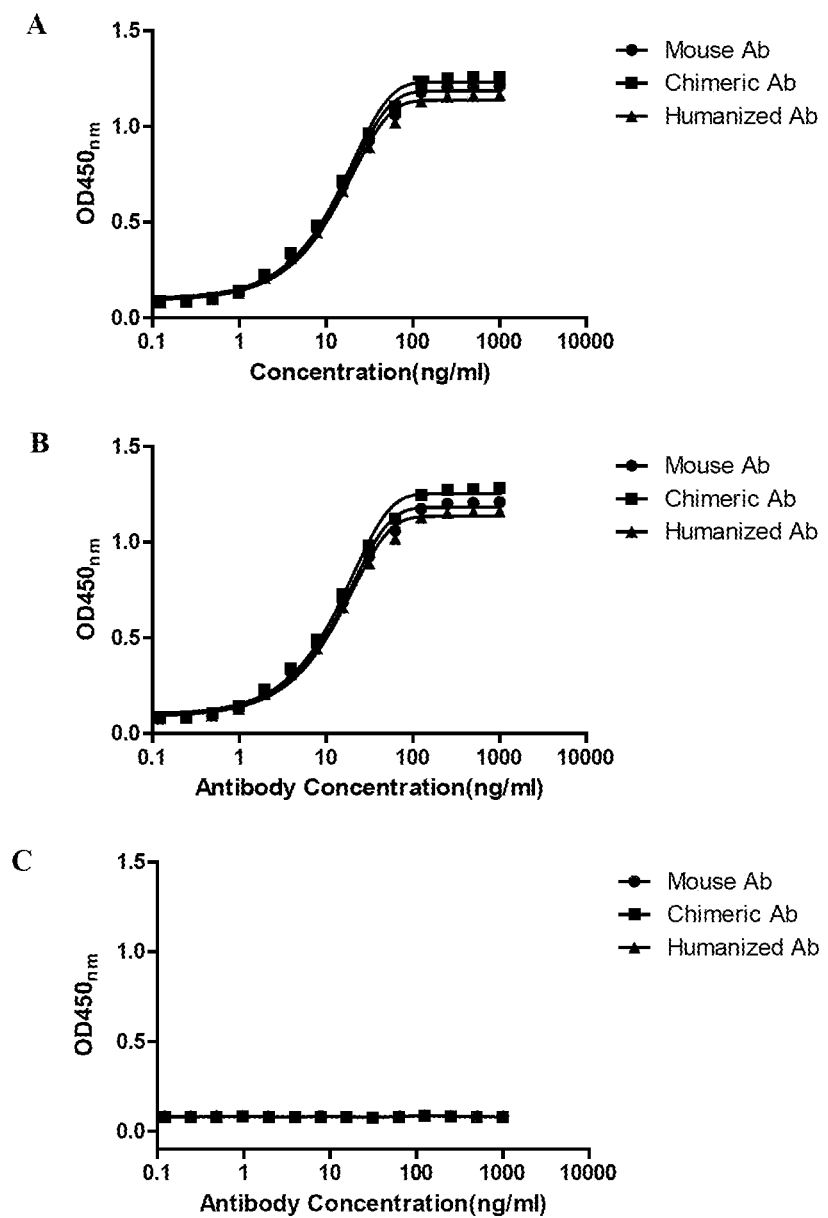
FIGS. 7A-7C show the results of experiments demonstrating that each of the anti-PD-1 antibodies 67D9 (mouse Ab), c67D9 (chimeric Ab), and hu67D9 (humanized Ab) binds to human PD-1-Fc (A) and Cynomolgus monkey PD-1-Fc (B), but not to mouse PD-1-Fc (C).

The mouse PD-1 and Cynomolgus monkey PD-1 were prepared as a Fc fusion protein using the same method for human PD-1-Fc in Example 1. Different concentrations of 67D9, c67D9, or hu67D9 were added to 96-well plates coated with human PD-1-Fc, mouse PD-1-Fc, or Cynomolgus monkey PD-1-Fc, followed by incubation at room temperature for 1 hour. After washing, HRP-conjugated goat anti-human kappa (for detecting c67D9 or hu67D9) or HRP-conjugated goat anti-mouse kappa (for detecting 67D9) was added and the plates were further incubated for 1 hour. Finally, TMB was added as a substrate for HRP, and the absorbance was measured at 450 nm. As shown in FIG. 7A-7C, each of the anti-PD-1 antibodies 67D9, c67D9, and hu67D9 bound to human PD-1-Fc and Cynomolgus monkey PD-1-Fc, but not to mouse PD-1-Fc.

Example 14. Thermal Stability Measurement

Differential scanning calormetry (DSC) measurement were performed to identify the apparent mid-point unfolding temperature (Tm). DSC was also used to measure the heat capacity of states and the excess heat associated with transitions that can be induced by temperature change. The integral of the excess heat capacity is the enthalpy for this process Major unfolding transitions appear as significant endothermic peaks.

Figure 8:
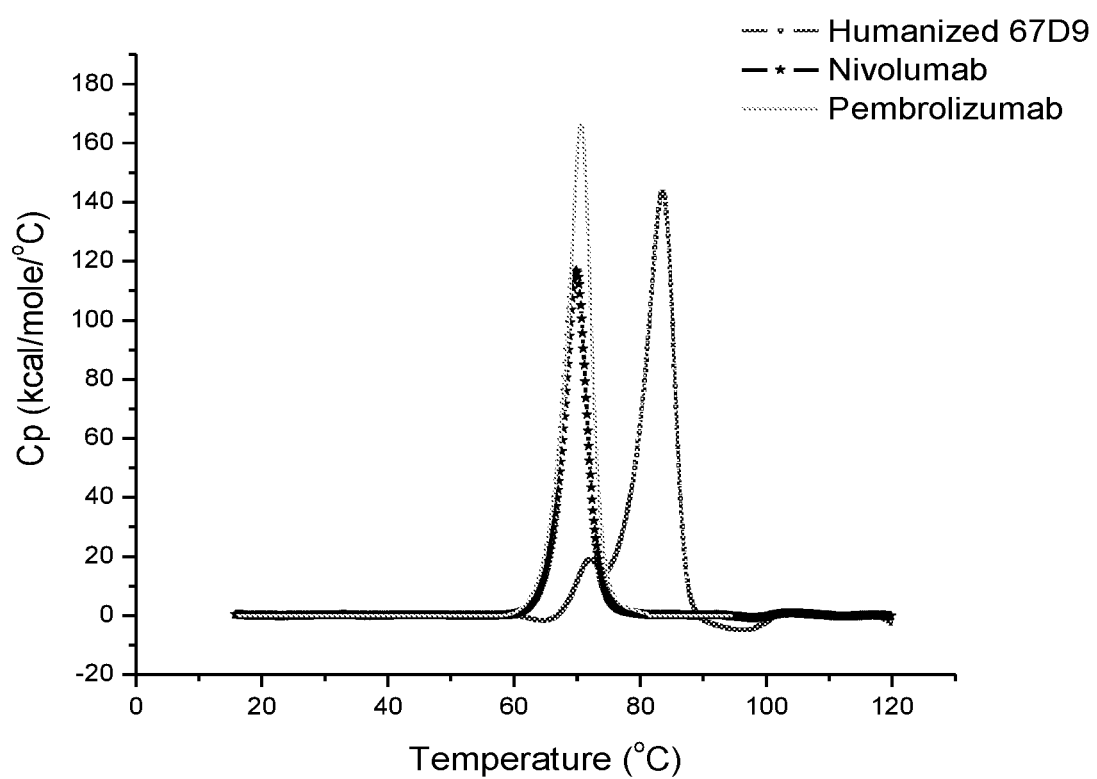
FIG. 8 shows DSC thermograms of Nivolumab, Pembrolizumab and hu67D9 (humanized 67D9) in PBS.

DSC experiments were performed using VP-DSC (Microcal, Northhampton, Mass.) for Nivolumab, Pembrolizumab, and hu67D9 solution at protein concentration of 0.5 mg/mL in PBS (pH 7.0). The mAbs were tested individually at a protein concentration of 0.5 mg/mL, and buffer control without protein was used as a reference. The samples were scanned from 10° C. to 120° C. at rate of 100° C./hour following an initial 10 min equilibration at 10° C. At least five buffer-buffer scans were performed to obtain baseline values and establish thermal history. The data were analyzed using Origin 7.0 (Origin-Lab, Northampton, Mass.). All thermograms were baseline corrected (linear connection) and fitted using the non-two-state model in Origin to obtain apparent midpoint temperatures (Tm) of unfolding and apparent enthalpy of unfolding (ΔH). As shown in FIG. 8 and Table 1, the unfolding temperature of hu67D9 is higher than Nivolumab and Pembrolizumab, suggesting that hu67D9 had better thermal stability compared with Nivolumab and Pembrolizumab.

TABLE 1

The apparent mid-point unfolding temperature and enthalpy of unfolding determined by DSC

| anti-PD-1 antibody | Tm (° C.) | ΔH (kcal) |
| --- | --- | --- |
| Pembrolizumab | 72.3 | 829 |
| Nivolumab | 69.2 | 581 |
| Humanized 67D9 | 83.5 | 929 |

Example 15. Kinetics and Affinity Measurements

The optical phenomenon of surface plasmon resonance (SPR) used by Biacore systems enables the detection and measurement of protein-protein interactions in real time, without the use of labels. The affinity of an antibody for its antigen may be determined by measuring the binding kinetics of the interaction.

In evaluation of kinetic and affinity constants, a PD-1-Fc fusion protein was immobilized and hu67D9 and Nivolumab were diluted into running buffer and analyzed.

Affinity constants were calculated from the ratio of the rate constants. As shown in FIG. 9 the KD of hu67D9 is 3.209E-12M, while the KD of Nivolumab is 2.116E-11M. These results indicate that hu67D9 binds to PD-1 with higher affinity than Nivolumab.

Example 16 Binding Activity with Cell Surface PD-1

Hu67D9 was tested for the ability to bind PD-1 expressed on transfected CHO-K1 (CHO/PD-1) cells using a standard flow cytometry assay.

A series dilution of hu67D9 or Nivolumab was incubated with the CHO/PD-1 cells respectively. After 1 hour incubation, the cells were washed and an FITC labelled anti human antibody was incubated for 1 hour. Then the cells were washed and the flow cytometric analysis was performed using a FACScan flow cytometry.

Figure 10:
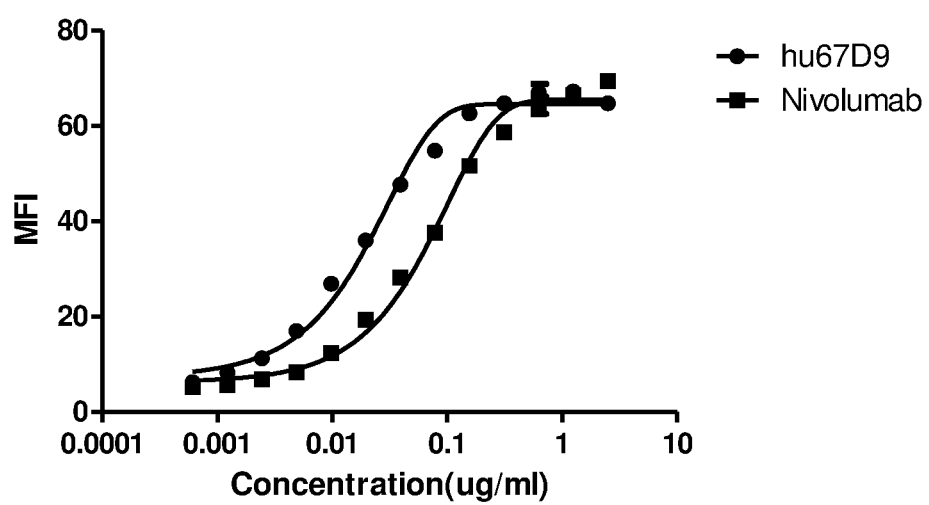
FIG. 10 shows the binding of Nivolumab and hu67D9 to PD-1 expressed on the cell surface.

As shown in FIG. 10, both hu67D9 and Nivolumab were able to bind to the PD-1 expressed on the cell surface. The $EC_{50}$ value of the hu67D9 is much lower than that of the Nivolumab which indicates that the hu67D9 binds to the cell surface PD-1 with higher affinity than Nivolumab.

Example 17 Binding Activity with Soluble PD-1

The specificity of the anti-PD-1 antibodies were examined by detecting their binding to soluble PD-1 using standard ELISA techniques.

Different concentrations of hu67D9 and Nivolumab were added to 96-well plates coated with PD-1-Fc, followed by incubation at room temperature for 2 hours. After washing, HRP-conjugated goat anti-human kappa was added and the plates were further incubated for 1 hour. Finally, TMB was added as a substrate for HRP, and the absorbance was measured at 450 nm.

Figure 11:
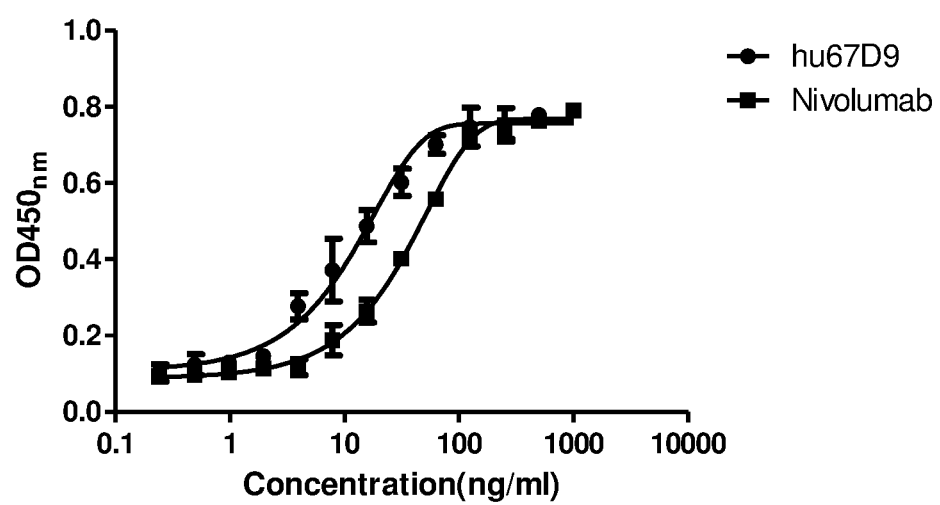
FIG. 11 shows the binding of Nivolumab and hu67D9 to soluble PD-1.

As shown in FIG. 11, both hu67D9 and Nivolumab were able to bind with the soluble PD-1. The $EC_{50}$ value of the hu67D9 is much lower than that of the Nivolumab which indicates that the hu67D9 binds to soluble PD-1 with higher affinity than Nivolumab.

Example 18 Competitive Binding Cell Surface PD-1 with Nivolumab

Hu67D9 was tested for the ability to compete binding of PD-1 expressed on transfected CHO-K1 (CHO/PD-1) cells with a flow cytometry assay.

A sub-saturating concentration of FITC labelled Nivolumab was incubated with series diluted hu67D9 or Nivolumab respectively. After 1 hour incubation, the cells were washed and flow cytometric analysis was performed using a FACScan flow cytometry.

Figure 12:
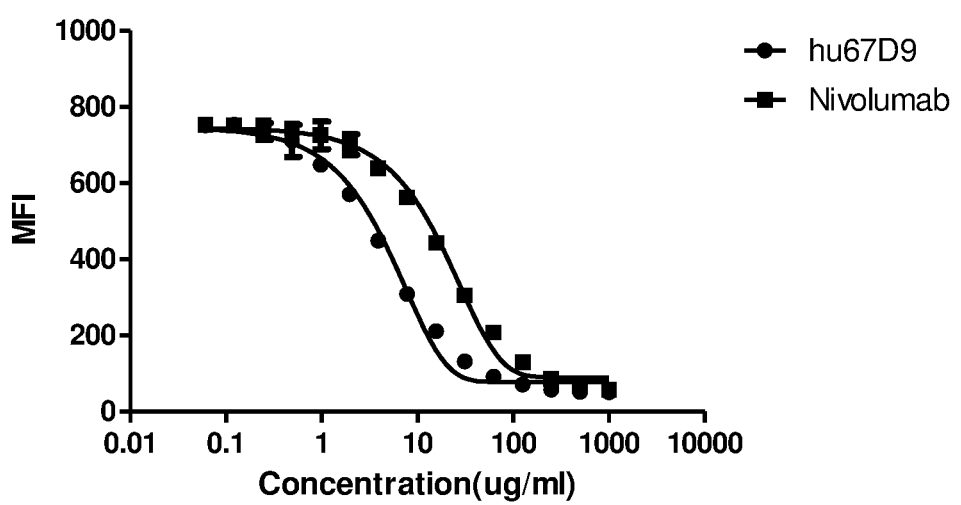
FIG. 12 shows the competitive binding of Nivolumab and hu67D9 to PD-1 expressed on the cell surface in the presence of FITC labelled Nivolumab.

As shown in FIG. 12, both hu67D9 and Nivolumab compete for the binding of the cell surface PD-1 with FITC labelled Nivolumab. The $IC_{50}$ value of the hu67D9 is much lower than that of the Nivolumab, which indicates that the hu67D9 competitively binds to the cell surface PD-1 with a higher affinity than Nivolumab.

Example 19 Competitive Binding Soluble PD1 with Nivolumab

Competitive binding soluble PD-1 activity of anti-PD-1 antibodies was examined using a standard ELISA technique.

A sub-saturated concentration of biotin labelled Nivolumab and series diluted hu67D9 or Nivolumab were added to 96-well plates coated with PD-1-Fc, followed by incubation at room temperature for 2 hours. After washing, HRP-avidin was added and the plate was further incubated for 1 hour. Finally, TMB was added as a substrate for HRP, and the absorbance was measured at 450 nm.

Figure 13:
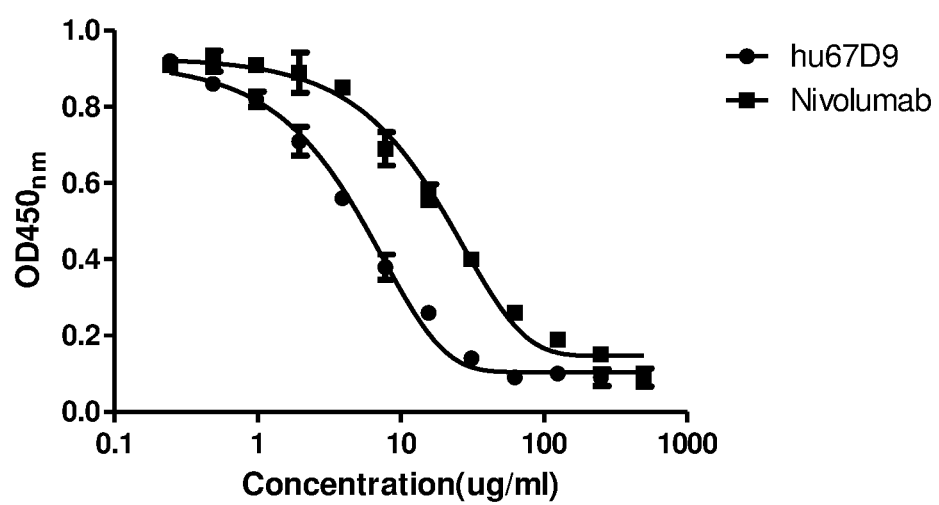
FIG. 13 shows the competitive binding of Nivolumab and hu67D9 to soluble PD1 in the presence of biotin labelled Nivolumab.

As shown in FIG. 13, both hu67D9 and Nivolumab compete with biotin labelled Nivolumab and bind to soluble PD-1. The $EC_{50}$ value of the hu67D9 is much lower than that of the Nivolumab which indicates that the hu67D9 competitively binds to soluble PD1 with higher affinity than Nivolumab.

Example 20 Competitive Binding Soluble PD1 with PD-L1

Competitive binding soluble PD1 with PD-L1 of anti-PD-1 antibodies was examined using a standard ELISA technique.

A sub-saturated concentration of biotin labelled PDL1-Fc and series diluted hu67D9 or Nivolumab were added to 96-well plates coated with PD-1-Fc, followed by incubation at room temperature for 2 hours. After washing, HRP-avidin was added and the plate was further incubated for 1 hour. Finally, TMB was added as a substrate for HRP, and the absorbance was measured at 450 nm.

Figure 14:
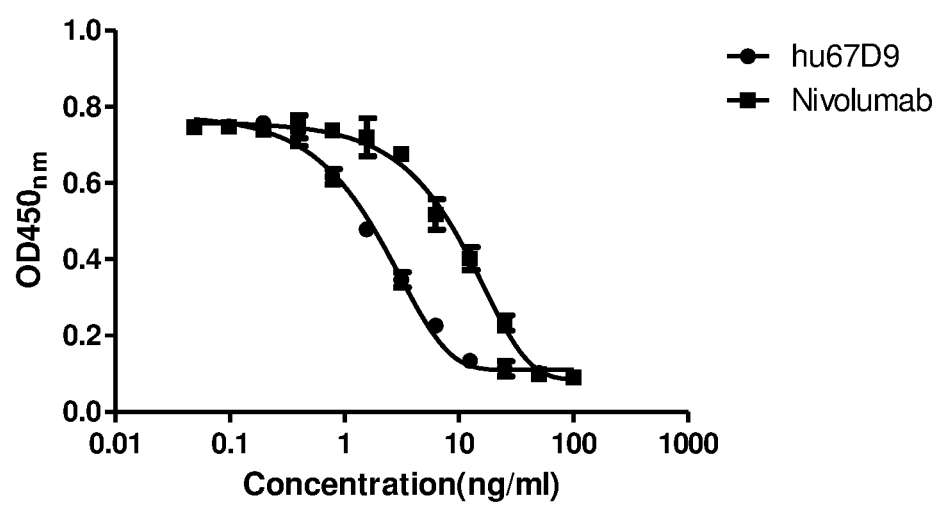
FIG. 14 shows the competitive binding of Nivolumab and hu67D9 to soluble PD1 in the presence of biotin labelled PDL1-Fc.

As shown in FIG. 14, both hu67D9 and Nivolumab compete with biotin labelled PDL1-Fc and bind to soluble PD-1. The $EC_{50}$ value of the hu67D9 is much lower than that of the Nivolumabwhich indicates that the hu67D9 competitively binds to soluble PD1 with higher affinity than Nivolumab.

The invention claimed is:

1. An anti-PD-1 monoclonal antibody or an antigen-binding fragment thereof, wherein said antibody or antigen-binding fragment thereof comprise a heavy chain variable region comprising SEQ ID NO: 1 (heavy chain CDR1), SEQ ID NO: 2 (heavy chain CDR2), SEQ ID NO: 3 (heavy chain CDR3) and a light chain variable region comprising SEQ ID NO: 4 (light chain CDR1), SEQ ID NO: 5 (light chain CDR2) and SEQ ID NO: 6 (light chain CDR3).

2. The monoclonal antibody of claim 1, wherein said heavy chain variable region comprising the amino acid sequence of SEQ ID NO:8 or SEQ ID NO:16 and said light chain variable region comprising the amino acid sequence of SEQ ID NO:10 or SEQ ID NO:18.

3. The monoclonal antibody of claim 1, wherein said antigen-binding fragment is a Fab, Fab', F(ab)$_2$, or F(ab')$_2$.

4. The monoclonal antibody of claim 1, wherein said antibody is a mouse, chimeric, or humanized antibody.

5. An isolated nucleic acid molecule which encodes the monoclonal antibody of claim 1.

6. An expression vector comprising the nucleic acid molecule of claim 5.

7. A host cell comprising the expression vector of claim 6.

8. A composition comprising the monoclonal antibody or antigen-binding fragment thereof of claim 1 and a pharmaceutically acceptable carrier.

9. An immunoconjugate comprising the monoclonal antibody or antigen-binding fragment thereof of claim 1 linked to a therapeutic agent.

10. The immunoconjugate of claim 9, wherein the therapeutic agent is a cytotoxin or a radioactive isotope.

11. A method of modulating an immune response in a subject comprising administering to the subject the antibody, or antigen-binding portion thereof, of claim 1 in an amount effective to modulate the immune response in the subject.

12. A method of inhibiting growth of tumor cells in a subject comprising administering to the subject the antibody, or antigen-binding fragment thereof, of claim 1 in an amount effective to inhibit growth of the tumor cells in the subject.

13. A method of treating an infectious disease in a subject comprising administering to the subject the antibody, or antigen-binding fragment thereof, of claim 1 in an amount effective to treat the infectious disease in the subject.

14. A method of manufacturing a medicament for modifying an immune response in a subject comprising employing the antibody, or antigen-binding portion thereof, of claim 1 in the manufacture of the medicament.

15. A method of manufacturing a medicament for inhibiting growth of tumor cells in a subject comprising employing the antibody, or antigen-binding portion thereof, of claim 1 in the manufacture of the medicament.

16. A method of manufacturing a medicament for treating an infectious disease in a subject comprising employing the antibody, or antigen-binding portion thereof, of claim 1 in the manufacture of the medicament.

* * * * *